US007003470B1

(12) United States Patent
Baker et al.

(10) Patent No.: US 7,003,470 B1
(45) Date of Patent: Feb. 21, 2006

(54) FUNDS FLOW SYSTEM FOR ACADEMIC HEALTH CENTERS

(75) Inventors: Robert J. Baker, Oak Brook, IL (US); David A. Burnett, Oak Brook, IL (US); Michael A. Geheb, Lake Oswego, OR (US)

(73) Assignee: University Healthsystem Consortium, Oak Brook, IL (US)

( * ) Notice: Subject to any disclaimer, the term of this patent is extended or adjusted under 35 U.S.C. 154(b) by 865 days.

(21) Appl. No.: 09/857,275

(22) PCT Filed: Oct. 30, 2000

(86) PCT No.: PCT/US00/29938

§ 371 (c)(1),
(2), (4) Date: Dec. 14, 2001

(87) PCT Pub. No.: WO01/33459

PCT Pub. Date: May 10, 2001

Related U.S. Application Data

(60) Provisional application No. 60/162,328, filed on Oct. 29, 1999.

(51) Int. Cl.
*G06F 17/00* (2006.01)
(52) U.S. Cl. .................................. 705/1; 705/2; 705/3
(58) Field of Classification Search .................. 705/1, 705/2, 3
See application file for complete search history.

(56) References Cited

U.S. PATENT DOCUMENTS

| | | | |
|---|---|---|---|
| 4,503,503 A | 3/1985 | Suzuki | |
| 5,638,519 A | 6/1997 | Haluska | |
| 5,704,044 A | 12/1997 | Tarter et al. | |
| 5,790,847 A | 8/1998 | Fisk et al. | |
| 5,799,286 A * | 8/1998 | Morgan et al. | 705/30 |
| 5,970,475 A | 10/1999 | Barnes et al. | |
| 6,014,640 A | 1/2000 | Bent | |
| 6,041,312 A | 3/2000 | Bickerton et al. | |
| 6,073,104 A | 6/2000 | Field | |
| 6,128,603 A * | 10/2000 | Dent et al. | 705/40 |

FOREIGN PATENT DOCUMENTS

JP    02002297896 A  * 10/2002

OTHER PUBLICATIONS

IBM Technical Disclosure Bulletin; Title: Electronic checkbook; TDB-ACC-No.: NNRD45292;; Dec. 2001.*

* cited by examiner

*Primary Examiner*—Elisca Pierre Eddy
(74) *Attorney, Agent, or Firm*—McDermott Will & Emery LLP

(57) ABSTRACT

A system and method for tracking and reporting the flow of funds between participants in an academic health center including a school of medicine, a hospital and a faculty clinical practice. The participants identify transactions between the participants and other entities. The participants then list all of the sources of funds and uses of funds for each department within an participant. The lists are analyzed to generate departmental sources of funds and uses of funds statements. The flow of funds include normalized hidden sources of funds, such as unreimbursed expenses. The lists are used to generate standardized and customized departmental statements. Using the standardized departmental statements and participant statements, departmental and participant ratios cab be generated. The ratios allow the participants to compare the participant's departments with each other as well as with other participant's departments and with other academic health centers.

12 Claims, 40 Drawing Sheets

| From/To | Index | U Index | S, PS | Description | Amount | Source |
|---|---|---|---|---|---|---|
| Hospital to FPP | 1 | A4 | S | ASC List | $1,479,000 | Hospital |
|  | 2 | B4 | S | Hospital Based Clinics | $1,192,973 | Hospital |
|  | 3 | B4 | S | Enterprise-wide Marketing | $254,753 | Hospital |
|  | 4 | B4 | S | Enterprise-wide Contracting | $66,949 | Hospital |
| Total |  |  |  |  | $2,993,675 |  |
| Hospital to FPP | 5 | D4 | PS | ASC List (includes gain sharing) | $5,266,183 | Hospital |
|  | 6 | D4 | PS | ASC List - ER Contract | $2,416,322 | Hospital |
| Total |  |  |  |  | $7,682,505 |  |
| FPP to Hospital | 7 | C | S | Differential in reimbursement for Indigent Care | $3,622,844 | E&Y |
| Hospital to SOM | 8 | A2 | S | ASC List | $708,079 | Hospital |
|  | 9 | A2 | S | ASC List - Other | $1,138,316 | Hospital |
| Total |  |  |  |  | $1,846,395 |  |
| State to Hospital | 10 | M2 | PS | Net Revenue for Indigent Care | $71,998,000 | Hospital |
|  | 11 | M2 | PS | Tobacco Tax Revenue | $1,163,000 | Hospital |
| Total |  |  |  |  | $73,161,000 |  |
| Hospital to State | 12 | L2 | S | Unreimbursed Indigent Care | $18,254,000 | Hospital |
|  |  | C,L2 |  | Additional loss due to resetting Indigent Care | $3,622,844 | E&Y |
| Total |  | L2 |  |  | $21,876,844 |  |
| Hospital to University | 13 | J2 | PS | Central Services Charged | $2,906,071 | Hospital |
| Hospital to TPA | 14 | NA | S | Enterprise-wide Marketing | $129,345 | Hospital |
|  | 15 | NA | S | Enterprise-wide Contracting | $113,004 | Hospital |
| Total |  |  |  |  | $242,349 |  |
| State to Hospital | 16 | K2 | S | Medi - Cal GME Funds | $10,000,000 | Hospital |
|  | 17 | K2 | S | Clinical Teaching Support | $8,493,272 | Hospital |
| Total |  |  |  |  | $18,493,272 |  |
| SOM to Hospital | 18 | A1 | S | Residency Program Support | $1,461,176 | SOM |
| FPP to University | 19 | J3 | PS | Central Services Charged | $611,000 | FPP |
| State to FPP | 20 | M3 | PS | Payments received for Indigent Care | $7,881,795 | FPP |
| FPP to State | 21 | L3 | S | Cost in excess of reimbursement for Indigent Care | $7,242,226 | FPP |
|  |  | C,L3 |  | Reimbursement gained in resetting Indigent Care | -$3,622,844 | E&Y |
| Total |  | L3 |  |  | $3,619,382 |  |
| FPP to SOM | 22 | A6 | S | Net Income Transfer | $47,893,151 | FPP |
|  | N/A | B6 | S | Pymt of Fac Sal for Res & Tchg from Clinical Mission | $10,600,00 | MGMA |
|  | 23 | G | S | Dean's Tax | $3,686,994 | FPP |
| Total |  |  |  |  | $62,180,145 |  |

FIG. 6A

| From/To | Index | U Index | S, PS | Description | Amount | Source |
|---|---|---|---|---|---|---|
| SOM to FPP | 24 | A5 | S | Faculty Salaries paid out of Clinical Funds | $40,545,651 | SOM |
| | 25 | A5 | S | Clinical Expenses | $8,610,980 | SOM |
| Total | | | | | $49,156,631 | |
| University to SOM | 26 | E1 | S | State Funds | $35,548,940 | SOM |
| | 27 | E1 | S | Expenses at Dean | $13,429,737 | SOM |
| Total | | | | | $48,978,677 | |
| SOM to University | 28 | I1 | PS | ICR Retained | $22,402,492 | SOM |
| | 29 | I1 | PS | Tuition and Fees Retained | $4,236,409 | SOM |
| | 30 | I1 | PS | Expenses at University | -$18,079,243 | SOM |
| Total | | | | | $8,559,658 | |

FIG. 6B

| Participant A | Internal Commerce | | | | | | |
|---|---|---|---|---|---|---|---|
| | Hospital to SOM | | Hospital to FCP | | SOM to FCP | SOM to Hospital | SOM to Hospital | FCP to Hospital | | FCP to SOM |
| PURCHASED SERVICE | | | | | | | |
| Physician Leadership | 1D2 | 1D4 | 3.6 | 1D5 | 1D1 | 1D3 | 1D6 |
| Physician Service | 2D2 | 2D4 | 2.8 | 2D5 | 2D1 | 2D3 | 2D6 |
| Physician Incentives | 3D2 | 3D4 | 1.3 | 3D5 | 3D1 | 3D3 | 3D6 |
| Nonphysician | 4D2 | 4D4 | | 4D5 | 4D1 | 4D3 | 4D6 |
| Supervision and Teaching | 5D2 | 5D4 | | 5D5 | 5D1 | 5D3 | 5D6 |

| To | From | Support ($000,000) | | | | | Payment for Services |
|---|---|---|---|---|---|---|---|
| | | Given ($) | Unreimbursed Expense ($) | Funds Generated Retained (FGR) > Centrally Provided ($) | Joint Venture | Total ($) | Cash and FGR < Centrally Provided |

Between Operating Activities

| To | From | Given ($) | Unreimb. Expense | FGR | JV | Total | Cash/FGR |
|---|---|---|---|---|---|---|---|
| Hospital | SOM | A1  1.5 | B1 | | | | D1 |
| SOM | Hospital | A2  1.8 | B2 | | | | D2 |
| Hospital | FCP | A3 | B3 | | | | D3 |
| FCP | Hospital | A4  1.5 | B4  1.5 | | C  3.6 | | D4  7.7 |
| FCP | SOM | A5  49.2 | B5 | | C | | D5 |
| SOM | FCP | A6  47.9 | B6  10.6 | G  3.7 | | | D6 |
| | subtotal to SOM | (1.0) | 10.6 | 3.7 | | 13.3 | |
| | subtotal to FCP | 2.8 | (9.1) | (3.7) | (3.6) | (13.6) | 7.7 |
| | subtotal to Hospital | (1.8) | (1.5) | | 3.6 | 0.3 | (7.7) |

Between University/VPHA/Health System and Operating Activities

| To | From | | | | | | |
|---|---|---|---|---|---|---|---|
| SOM | University/VPHA/Health System | E1  49.0 | H1 | I1  8.6 | | | |
| University/VPHA/Health System | SOM | F1 | | | | | J1  18.1 |
| Hospital | University/VPHA/Health System | E2 | H2 | I2 | | | J2  2.9 |
| University/VPHA/Health System | Hospital | F2 | | | | | J3  0.6 |
| FCP | University/VPHA/Health System | E3 | H3 | I3 | | | |
| University/VPHA/Health System | FCP | | | | | | |
| | subtotal to SOM | 49.0 | - | (8.6) | | 40.4 | (18.1) |
| | subtotal to FCP | - | - | - | | - | (0.6) |
| | subtotal to Hospital | - | - | - | | - | (2.9) |
| | subtotal to University/VPHA/Health System | (49.0) | - | 8.6 | | (40.4) | 21.6 |

Between State/County/Community and Operating Activities

| To | From | | | | | | |
|---|---|---|---|---|---|---|---|
| State/County/Community | Hospital | K2  18.5 | L2  21.9 | | | | |
| Hospital | State/County/Community | | | | | | |
| State/County/Community | FCP | | L3  3.6 | | | | M2  73.2 |
| FCP | State/County/Community | | | | | | M3  7.9 |
| | subtotal to FCP | - | (3.6) | | | (3.6) | 7.9 |
| | subtotal to Hospital | 18.5 | (21.9) | | | (3.4) | 73.2 |
| | subtotal to State/County/Community | (18.5) | 25.5 | | | 7.0 | (81.1) |

| | | Given | Unreimb | FGR | JV | Total | Cash/FGR |
|---|---|---|---|---|---|---|---|
| SOM | Net Support | 48.0 | 10.6 | (4.9) | - | 53.7 | |
| | Net Services Purchased from (sold) | | | | | | (18.1) |
| FCP | Net Support | 2.8 | (12.7) | (3.7) | (3.6) | (17.2) | |
| | Net Services Purchased from (sold) | | | | | | 15.0 |
| Hospital | Net Support | 16.7 | (23.4) | - | 3.6 | (3.1) | |
| | Net Services Purchased from (sold) | | | | | | 62.6 |
| University/VPHA/Health System | Net Support | (49.0) | - | 8.6 | - | (40.4) | |
| | Net Services Purchased from (sold) | | | | | | 21.6 |
| State/County/Community | Net Support | (18.5) | 25.5 | - | - | 7.0 | |
| | Net Services Purchased from (sold) | | | | | | (81.1) |
| | CHECK AREA | - | - | - | - | - | - |

Programs and Services

| Index | From/To | S, PS | Type | Category | Amount | Supporting Schedule | Description | Source /Contact |
|---|---|---|---|---|---|---|---|---|
| 1, A4 | Hospital to FCP | S | Given | Programs & Services | $13.3 M | | State Appropriations & State Paid Benefits to Model Clinics at Hospital's discretion | Steering Committee |
| | | | | | $11.1M $2.2M | | State Appropriations Passed Through (Cash) Benefits (NonCash) | |
| | | | | | Not Quantified | | Joint Venture Clinic Operations<br>• Sharing Formula 75/25 losses; • 50/50 profit<br>• Annual reconciliation vs. Quarterly (Cash Flow)<br>• Expected vs. Actual Collections/MD Pro Fees (Sharing Formula)<br>• Low Indirect Cost/Overhead Rate<br>• Payment for Amb Care Medical Directorships | |
| 2, B4 | Hospital to FCP | S | Unreimbursed Expenses | Programs & Services | $.4M | | Billing - 8% of net revenue (NonCash)<br>A/R Funding - 5% for 80 days (NonCash) | Pat O'Leary |
| 3, 1D4 | Hospital to FCP | PS | Given | Programs & Services | $4.72M | A | Contracts b/t Hospital and COM Clinical Depts/Faculty<br>• Medical Directorships, Chiefs of Svc, Prgm Dirs | Hospital Pymt Report/Tony Ferrara/Steering Committee |
| | | | | | $4.0M $.72M | | Salaries (Cash)<br>Benefits - estimated at 18% (NonCash) | |
| 4, A4 | Hospital to FCP | S | Given | Programs & Services | $3.2M | A | Contracts b/t Hospital and COM Clinical Depts/Faculty<br>• Investment in Programs & Services | Hospital Pymt Report/Tony Ferrara/Steering Committee |
| | | | | | $2.7M $.5M | | Salaries (Cash)<br>Benefits - estimated at 18% (NonCash) | |

FIG. 10A-1

Programs and Services

| | | | | | |
|---|---|---|---|---|---|
| 5, B3 | FCP to Hospital | S | Unreimbursed Expenses | Programs & Services | $2M | A | Unreimbursed Faculty Effort benefiting Hospital Unfunded Medical Direction Salaries & Benefits (NonCash) | Hospital Pymt Report/Tony Ferrara/Steering Committee |
| N/A | Hospital & FCP | S | | Programs & Services | Not Quantified | | Inherent Characteristics of the AME: • Lack of Standardization/Equipment | Steering Committee |

FIG. 10A-2

OVCHS/Strategic Investment Fund

| Index | From/To | S, PS | Type | Category | Amount | Supporting Schedule | Description | Source/Contact |
|---|---|---|---|---|---|---|---|---|
| 1, N/A | Hospital to OVCHS | S | | OVCHS/ SIF | $8.9M | B | Funding of Strategic Investment Fund ($10.3M) net of expenditures on Hospital Projects | |
| 2, B4 | Hospital to FCP | S | Unreimbursed Expenses | OVCHS/ SIF | $1M | | Hospital funds OVCHS office in the amount of $4.2M - estimate is that OVCHS benefits Hospital 75% and FCP 25% | |
| 3, A4 | OVCHS to FCP | S | Given | OVCHS/ SIF | $1.9M $1.5M $.25M $.15M | B | SIF Expenditures<br>Faculty Salaries (Cash)<br>Faculty Benefits - estimated at 18% (NonCash)<br>Other Expenditures (Cash) | |
| 4, A2 | OVCHS to COM | S | Given | OVCHS/ SIF | $2.5M $.8M $.15M $1.5M | B | SIF Expenditures<br>Faculty Salaries (Cash)<br>Faculty Benefits - estimated at 18% (NonCash)<br>Other Expenditures (Cash) | |
| 5, D3 | FCP to OVCHS | PS | | OVCHS/ SIF | $.5M | | Funding from MDs for marketing (Cash) | |

FY 98

| | | | | | | | | |
|---|---|---|---|---|---|---|---|---|
| N/A | Hospital to COM/ | S | | OVCHS/ SIF | Not Quantified | | Funding of New Ambulatory Care Center • $20 million down through short term bond | |

FIG. 10B

Public Aid/Prison Population

| Index | To/From | S, PS | Type | Category | Amount | Supporting Schedule | Description | Source/Contact |
|---|---|---|---|---|---|---|---|---|
| 1, C | FCP to Hospital | S | Unreimbursed Expenses | Public Aid/ Prison Pop | $10.4M | C | Different Levels of Reimbursement for:<br>• Public Aid<br>• Prison Pop | Calculation |
| 2, M2 | State to Hospital | Pymt for Clin Svcs | | Public Aid/ Prison Pop | $84.7M | C | State funding for:<br>• Public Aid<br>• Prison Pop | Audited Financial Stmts; UIC Hospital Records |
| | | | | | $55.6 | | Public Aid Reimbursement (Cash) | |
| | | | | | $29.1 | | Payments on Behalf of the System attributed to Public Aid/Prison Pop Costs- Benefits (NonCash) | |
| 3, L2 | Hospital to State | S | Unreimbursed Expenses Out | | $11.2M | C | Unreimbursed expenses/shortfall related to Public Aid/Prison Population Before Reimbursement Reset | |
| | | | | | $10.4M | | Reimbursement Foregone Under Reset | |
| | | | | | $21.6M | | Unreimbursed expenses after Reimbursement Reset | |
| 4, M3 | State to FCP | Pymt for Clin Svcs | | Public Aid/ Prison Pop | $11.1M | C | Public Aid Reimbursement (Cash) | Audited Financial Stmts/ Hosp Amt Accts |
| 5, L3 | FCP to State | S | Unreimbursed Expenses Out | Public Aid/ Prison Pop | $16.7M | C | Unreimbursed expenses/shortfall related to Public Aid/Prison Pop Before Reimbursement Reset | |
| | | | | | ($10.4M) | | Reimbursement Gained Under Reset | |
| | | | | | $6.3M | | Unreimbursed expenses after Reimbursement Reset | |

FIG. 10C

Research and Teaching

| Index | To/From | S, PS | Type | Category | Amount | Supporting Schedule | Description | Source/Contact |
|---|---|---|---|---|---|---|---|---|
| | Hospital to COM | S | Unreimbursed Expenses | Research | $ ___ | | Clerical/other support for research | |
| | COM to Hospital | PS | | Research | $ ___ | | Hospital services for research (ie., beds, labs, x-rays, etc.) (Cash) | |
| 1, G | FCP to COM | S | Given | Research & Teaching | $1.5M | | Dean's Tax (Cash) - Net of Services Provided | |
| 2, B6 | FCP to COM | S | Unreimbursed Expenses | Research & Teaching | $1.6M | | Payment of Faculty Salaries & Benefits for Research Effort | |
| N/A | FCP to COM | S | Unreimbursed Expenses | Research & Teaching | To Be Noted - Not Quantified at Present | | Payment of Nonfaculty Salaries for Research & Teaching Effort | |
| 3, B3 | FCP to Hospital | S | Unreimbursed Expenses | Research & Teaching | $1.7M | | Unreimbursed Faculty Effort benefiting Hospital • Committee Meetings (Public Svc - Hospital) | |
| 4, B1 | COM to Hospital | S | Unreimbursed Expenses | Residency Program | $10.7M | | Unreimbursed Faculty Effort benefiting Hospital • Supervision of House Staff | |

Centrally Provided

| Index | To/From | S, PS | Type | Category | Amount | Description | Source/Contact |
|---|---|---|---|---|---|---|---|
| 1; E1 | Univ/State to COM (includes Basic Sci Depts) | S | | Cent Prov | $37.2M | State Appropriations to Department for Research & Teaching (Cash) | |
| | | | | | $4.5M | plus State Paid Benefits (Noncash) | |
| | | | | Subtotal | $41.7M | | |
| 2; K2 | Univ/State to Hospital | S | | Cent Prov | $44.6M | State Appropriations (Cash) | AFS, UIC Hospital |
| 3; F2 | Hospital | S | | Cent Prov | $2.8M | Support for other Colleges - i.e., Health Professions, Pharmacy, Nursing (Cash) | Hospital Pymt Report |
| 4; N/A | Hospital to Univ/State | PS | | Cent Prov | $.3M | Purchased Services from Nursing & Dentistry Colleges (Cash) | Hospital Pymt Report |
| 5; H2 | Univ/State to Hosp | S | | Cent Prov | $9.9M | FY 97 On Behalf Payments for Maintenance, Utilities and A&G (Noncash) | AFS, UIC Hospital |
| 6; K2 | Univ/State to OVCHS | S | | Cent Prov | $1.4M | State Funding - Includes Excellence in Academics (Cash) | |
| 7; J2 | Hospital to Univ/State | PS | | Cent Prov | $7.7M | Central Service Charges (i.e., overhead - Univ/Campus Admin) ($11.9M per AFS - 4.2M to OVCHS) (Cash) | AFS |
| 8; J1 | COM to Univ/State | Pymt for Central Svcs | | Cent Prov | $14.8M | Funds Generated Retained (Teaching, Research) for Central Service (Clinical Depts - 8.5M; Basic Science Depts - $6.3M) | |
| 9; H1 | Univ/State to COM | S | | Cent Prov | $1.7M | Services provided in excess of Funds Generated Retained (Noncash) | |
| 10; N/A | FCP to COM | Pymt for Central Svcs | | Cent Prov | $3M | Dean's tax applied toward Svcs provided by the Dean for FPP (Cash) | |

Table of Purchased Services and Support by Hospital

| | (A) Cash<br>Purchased Services by Hospital - Cash | (A1) Non-Cash<br>Purchased Services by Hospital - Benefits | (B) Non-Cash<br>MSP Support to Hospital | (B1) Non-Cash<br>MSP Support to Hospital (Benefits) | (A) + (B) Cash & Non-Cash<br>Total Salary Value of Svcs Provided to Hospital | (A1) + (B1) Non-Cash<br>Total Benefits Value of Svcs Provided to Hospital |
|---|---|---|---|---|---|---|
| Anesthesiology | $ 661,000 | 118,980 | - | - | $ 661,000 | 118,980 |
| Dermatology | 44,945 | 8,090 | 192,055 | 34,570 | 237,000 | 42,660 |
| Emergency Medicine | 117,000 | 21,060 | - | - | 117,000 | 21,060 |
| Family Medicine | 52,268 | 9,408 | 732 | 132 | 53,000 | 9,540 |
| General and Internal | 854,004 | 153,721 | 75,996 | 13,679 | 930,000 | 167,400 |
| Neurology | 126,502 | 22,770 | 131,498 | 23,670 | 258,000 | 46,440 |
| Neuro | 50,500 | 9,090 | 70,500 | 12,690 | 121,000 | 21,780 |
| OB/Gyn | 241,000 | 43,380 | - | - | 241,000 | 43,380 |
| Ophthalmology | 21,816 | 3,927 | 280,184 | 50,433 | 302,000 | 54,360 |
| Orthopedic | 105,550 | 18,999 | 24,450 | 4,401 | 130,000 | 23,400 |
| Otorhinolaryngology | 33,000 | 5,940 | 197,000 | 35,460 | 230,000 | 41,400 |
| Pathology | 267,000 | 48,060 | - | - | 267,000 | 48,060 |
| General Peds | 337,680 | 60,782 | 257,320 | 46,318 | 595,000 | 107,100 |
| Psychiatry | 216,000 | 38,880 | - | - | 216,000 | 38,880 |
| Radiation Oncology | 25,000 | 4,500 | 35,000 | 6,300 | 60,000 | 10,800 |
| Radiology | 209,230 | 37,661 | 250,770 | 45,139 | 460,000 | 82,800 |
| Physical Medicine | 122,000 | 21,960 | - | - | 122,000 | 21,960 |
| General Surg | 442,000 | 79,560 | - | - | 442,000 | 79,560 |
| Surgical Oncology | 38,700 | 6,966 | 24,300 | 4,374 | 63,000 | 11,340 |
| Urology | 67,167 | 12,090 | 169,833 | 30,570 | 237,000 | 42,660 |
| Total | $ 4,032,362 | $ 725,825 | $ 1,709,638 | $ 307,735 | $ 5,742,000 | $ 1,033,560 |

FIG. 11A

Table of Purchased Services and Support by Hospital

| | (C) Cash<br>Hospital Support to MSP | (C1) Non-Cash<br>Hospital Support to MSP (Benefits) | (A) + (C) Cash<br>Hospital Cash Pymts to MSP | (A1) + (C1) Cash<br>Hospital Non-Cash Payments to MSP | (A) + (A1) + (C) + (C1) Cash & Non-Cash<br>Total Hospital Cash & Non-Cash Payments to MSP |
|---|---|---|---|---|---|
| Anesthesiology | $ 158,822 | 28,588 | $ 819,822 | 147,568 | $ 967,3 |
| Dermatology | - | - | 44,945 | 8,090 | 53,0 |
| Emergency Medicine | 1,014,183 | 182,553 | 1,131,183 | 203,613 | 1,334,2 |
| Family Medicine | - | - | 52,268 | 9,408 | 61,6 |
| General and Internal | - | - | 854,004 | 153,721 | 1,007,2 |
| Neurology | - | - | 126,502 | 22,770 | 149,2 |
| Neuro | - | - | 50,500 | 9,090 | 59,5 |
| OB/Gyn | 30,500 | 5,490 | 271,500 | 48,870 | 320,3 |
| Ophthalmology | - | - | 21,816 | 3,927 | 25,7 |
| Orthopedic | - | - | 105,550 | 18,999 | 124,5 |
| Otorhinolaryngology | - | - | 33,000 | 5,940 | 38,9 |
| Pathology | 1,132,595 | 203,867 | 1,399,595 | 251,927 | 1,651,5 |
| General Peds | - | - | 337,680 | 60,782 | 398,4 |
| Psychiatry | 2,450 | 441 | 218,450 | 39,321 | 257,7 |
| Radiation Oncology | - | - | 25,000 | 4,500 | 29,5 |
| Radiology | - | - | 209,230 | 37,661 | 246,8 |
| Physical Medicine | 7,050 | 1,269 | 129,050 | 23,229 | 152,2 |
| General Surg | 341,028 | 61,385 | 783,028 | 140,945 | 923,9 |
| Surgical Oncology | - | - | 38,700 | 6,966 | 45,6 |
| Urology | - | - | 67,167 | 12,090 | 79,2 |
| Total | $ 2,686,628 | $ 483,593 | $ 6,718,990 | $ 1,206,418 | $ 7,928,4 |
| Total Cash Payments per Salary Schedule (excludes amb care med directorships) | | | $ 6,687,990 | 1,203,838 | 7,891,8 |
| Variance | | | $ 31,000 | | $ 36,5 |

FIG. 11B

| | | | Strategic Investment Fund | | | | | | | |
|---|---|---|---|---|---|---|---|---|---|---|
| Expenditures / Transfers Out | Department attributed to for Funds Flow | UIC Attribution by Department | Description | SOM | Hospital | MSP | Faculty Salaries SOM | All other SOM | Faculty Salaries MSP | All other MSP | Total |
| Administration | Administration (OVCHS) | Miscellaneous | CON Consultants (various projects) | - | 1,100 | 1,100 | | | | | |
| | Ambulatory Services | Ambulatory Care Initiatives | CON Consultants (DMW/Vinson/HFPB) | - | 12,500 | 12,500 | | | | | |
| | Ambulatory Services | Ambulatory Care Initiatives | AirRights/City (Neal) | - | 12,500 | 12,500 | | | | | |
| | Ambulatory Services | Ambulatory Care Initiatives | Misc Amb Care Expenses | - | 10,700 | 10,700 | | | | | |
| | | | | - | 36,800 | 36,800 | | | | | |
| Family Medicine | Family Medicine | Ambulatory Care Initiatives | Family Practice | - | - | 95,500 | | | | 95,500 | |
| | | | | - | - | 95,500 | | | | 95,500 | |
| General Surg | General Surg | Transplant Initiatives | Heart-Lung Transplant (Massad, Fac Sal) | - | - | 429,500 | | | 667,521 | | |
| | | | Admin alloc | - | - | 429,500 | | | 667,521 | (238,021) | |
| | General and Internal Medic | Oncology Initiatives | Transplant and Cell Facility | 246,900 | | - | 148,234 | | | | |
| | General and Internal Medic | Oncology Initiatives | Gene Therapy Center (Research) | 274,200 | | - | 166,418 | | | | |
| | General and Internal Medic | Oncology Initiatives | Med Onc Gottlieb | | | 12,200 | | | | | |
| | General and Internal Medic | Oncology Initiatives | Medical Oncology (Research) | 243,400 | | - | 125,692 | | | | |
| | General and Internal Medic | Oncology Initiatives | Bone Marrow Transplant (Research) | 380,200 | | - | 349,479 | | | | |
| | General and Internal Medic | Transplant Initiatives | DDLC | | | 376,300 | | | 314,459 | | |
| Total Medicine | | | Admin alloc | 1,144,700 | - | 388,500 | 789,823 | 354,877 | 314,459 | 74,041 | |
| Hospital | Hospital | Oncology Initiatives | Bone Marrow Remodeling | | 1,090,00 | - | | | | | |
| | Hospital | EEI Initiatives | Facility Renovation | | 49,800 | - | | | | | |
| | Hospital | Transplant Initiatives | Hospital Transplant FY95-96 | | 300,000 | - | | | | | |
| | | | | | 1,439,800 | - | | | | | |
| Neurology | Neurology | Neuroscience Initiatives | Epilepsy Clinical Prog (Heir, Fac Sal) | - | - | 206,200 | | | 44,526 | | |
| | | | Admin alloc | - | - | 206,200 | | | 44,526 | 161,674 | |

FIG. 12A-1

Strategic Investment Fund

| Department attributed to for Funds Flow | UIC Attribution by Department | Description | SOM | Hospital | MSP | Faculty Salaries SOM | All other SOM | Faculty Salaries MSP | All other MSP | Total |
|---|---|---|---|---|---|---|---|---|---|---|
| Expenditures / Transfers Out: | | | | | | | | | | |
| Neuro | | | | | | | | | | |
| Neuro Surgery | Neuroscience Initiatives | Stroke Clinical Program (Ausman, Fac Sal) | | - | 82,100 | 69,697 | | 41,651 | | |
| Neuro Surgery | Neuroscience Initiatives | Imaging Collaboratory (Sadler, Fac Sal) | 191,100 | - | - | | 121,403 | | 40,449 | |
| | | Admin alloc | 191,100 | - | 82,100 | 69,697 | 121,403 | 41,651 | 40,449 | |
| OB/GYN | | | | | | | | | | |
| OB/GYN | Women's/Children's Initiatives | Department of OB/GYN (Fac Sal) | | - | 288,800 | | | 279,193 | 9,607 | |
| | | Admin alloc | | - | 288,800 | | | 279,193 | 9,607 | |
| General Peds | Genetics Program (Peds) | Genetics Program (Peds, Fac Sal) | | - | 63,400 | | | 59,559 | 3,841 | |
| Total Pediatrics | | Admin alloc | | - | 63,400 | | | 59,559 | 3,841 | |
| Psychiatry | Neuroscience Initiatives | PI Remodeling (Costa) | 1,000,000 | - | - | - | 1,000,000 | - | - | |
| | | | 1,000,000 | - | - | - | 1,000,000 | - | - | |
| Specialized Cancer Center | Oncology Initiatives | Cancer Center (Beck) | 497,700 | - | - | - | 497,700 | - | - | |
| | | | 497,700 | - | - | - | 497,700 | - | - | |
| Surgical Oncology | Oncology Initiatives | Surgical Oncology (Fac Sal) | | - | 125,200 | | | 123,226 | 1,974 | |
| | | Admin alloc | | - | 125,200 | | | 123,226 | 1,974 | |
| Total Expenditures / Transfers Out: | | | 2,833,500 | 1,476,600 | 1,716,000 | 859,520 | 1,973,980 | 1,530,135 | 149,065 | 6,026,100 |

A) ANESTHESIOLOGY (107)*
B) DERMATOLOGY (71)*
C) EMERGENCY MEDICINE (58)*
D) FAMILY MEDICINE (106)*
E) INTERNAL MEDICINE (123)*
- GENERAL INTERNAL MEDICINE
- CARDIOLOGY*
- ENDOCRINOLGY/METABOLISM
- GERIATRICS
- GASTROENTEROLOGY*
- HEMATOLOGY/ONCOLOGY*
- INFECTIOUS DISEASES
- NEPHROLOGY
- PULMONARY DISEASE*
- RHEUMATOLOGY

F) NEUROLOGY (103)*

G) OBSTETRICS/GYNECOLOGY (123)*
- GYNECOLOGICAL ONCOLOGY
- MATERNAL AND FETAL MEDICINE
- REPRODUCTIVE ENDOCRINOLOGY

H) PEDIATRICS (124)*
- GENERAL PEDIATRICS
- PEDIATRIC CARDIOLOGY
- PEDIATRIC CRITICAL CARE
- PEDIATRIC ENDOCRINOLOGY
- PEDIATRIC GASTROENTEROLOGY
- PEDIATRIC NEONATAL MEDICINE
- PEDIATRIC NEUROLOGY
- PEDIATRIC PULMONOLOGY

I) PHYSICAL MEDICINE/REHABILITATION MEDICINE (62)*
J) PSYCHIATRY (123)*
K) RADIOLOGY*
- NUCLEAR MEDICINE
- RADIATION ONCOLOGY (64)*
- DIAGNOSTIC RADIOLOGY (111)*

L) PATHOLOGY (124)*
- ANATOMIC PATHOLOGY
- CLINICAL PATHOLOGY
- BASIC SCIENCE

M) SURGERY*
- CARDIOVASCULAR SURGERY
- GENERAL SURGERY
- NEUROLOGICAL SURGERY (70)*
- OPHTHALMOLOGY (97)*
- ORTHOPEDIC SURGERY (84)*
- OTORHINOLARYNGOLOGY (79)*
- PEDIATRIC SURGERY
- PLASTIC SURGERY
- UROLOGY (63)
- VASCULAR/THORACIC SURGERY

FIG. 13

Participant
Funds Flow Statement - FY 199x
Clinical Area

| | A | B | C | D |
|---|---|---|---|---|
| | School of Medicine | | Faculty Clinical Practice | Total |
| | Externally Funded Research | Other Academic | | |

| SOURCES OF FUNDS | | A | B | C | D |
|---|---|---|---|---|---|
| | Funds Generated - External | | | | |
| 1 | Net Patient Care Revenue | $ | $ | $ 5,701,054 | $ 5,701,054 |
| 2 | DER - Federal | 1,139,952 | | | 1,139,552 |
| 3 | DER - NonFederal | 652,962 | | | 652,962 |
| 4 | ICR - Federal | 444,544 | (400) | | 443,740 |
| 5 | ICR - NonFederal | 109,623 | (803) | | 109,632 |
| 6 | Tuition and Fees | | 317,952 | | 317,952 |
| 7 | Direct Paid Salaries | | | | |
| 8 | Other External Generated | | 75,656 | 80,013 | 155,669 |
| 8a | Other Indigent | | | 398,166 | 398,166 |
| 9 | UHC Database Adjustment | | | | |
| 10 | Subtotal | 2,347,080 | 392,405 | 6,179,233 | 8,918,718 |
| | Funds Generated - Internal | | | | |
| 11 | From the Hospital | | | 163,100 | 163,100 |
| 12 | Other | | | | |
| 13 | From Hospital - Unreimbursed Expenses | | | | |
| 14 | Other - Unreimbursed Expenses | | | | |
| 15 | UHC Database Adjustment | | | | |
| 16 | Subtotal | | | 163,100 | 163,100 |
| 17 | Total Funds Generated | 2,347,080 | 392,405 | 6,342,333 | 9,081,818 |

FIG. 15A

| | | A | B | C | D |
|---|---|---|---|---|---|
| | | School of Medicine | | Faculty Clinical Practice | Total |
| | SOURCES OF FUNDS | Externally Funded Research | Other Academic | | |
| 18 | Funds Invested | | | | |
| 19 | Institutional Investment | | | | |
| 20 | Funds Provided | | | | |
| 21 | From University | | | | |
| | From Health System | | | | |
| | From Dean | | 1,229,175 | | 1,229,175 |
| | Other | | | | |
| 22 | Subtotal | | 1,229,175 | | 1,229,175 |
| | Unreimbursed Expenses Incurred on Behalf of Dept | | | | |
| 23 | University | 131,146 | 485,432 | | 616,578 |
| 24 | Health System | | | | |
| 25 | Dean | 103,286 | 382,310 | | 485,596 |
| 26 | Other | | | | |
| 27 | Subtotal | 234,433 | 867,742 | | 1,102,175 |
| | Funds Generated Retained | | | | |
| 28 | Research/ICR Retained | (357,731) | 803 | | (356,928) |
| 29 | Teaching | | (192,208) | | (192,208) |
| 30 | Clinical | | | (328,743) | (328,743) |
| 31 | Subtotal | (357,731) | (191,405) | (328,743) | (877,879) |
| | Support Between AMC Operating Units | | | | |
| 32 | From Hospital | | | 700,000 | 531,718 |
| 32a | Indigent Care | | (168,282) | (398,166) | (398,166) |
| 33 | Other | | | | |
| 34 | From Hospital - Unreimbursed Expense | | | | |
| 35 | Other - Unreimbursed Expense | | | | |
| 36 | UHC Database Adjustment | | | | |
| 37 | Subtotal | | (168,282) | 301,834 | 133,552 |

FIG. 15B-1

| SOURCES OF FUNDS | | A School of Medicine | B | C Faculty Clinical Practice | D Total |
|---|---|---|---|---|---|
| | | Externally Funded Research | Other Academic | | |
| | Departmental Investment | | | | |
| 38 | Across Missions | (74,124) | 739,069 | (1,115,706) | (450,761) |
| 39 | Across Missions - *Unreimbursed Expenses* | | 312,620 | (312,620) | - |
| 40 | Other | | 156,878 | | 156,878 |
| 41 | *Subtotal* | (74,124) | 1,208,568 | (1,428,327) | (293,883) |
| 42 | Total Funds Invested | (194,422) | 2,945,798 | (1,455,236) | 1,293,140 |
| 43 | Total Sources of Funds | 2,149,658 | 3,338,203 | 4,887,097 | 10,374,958 |

FIG. 15B-2

| | SOURCES OF FUNDS | A School of Medicine — Externally Funded Research | B School of Medicine — Other Academic | C Faculty Clinical Practice | D Total |
|---|---|---|---|---|---|
| | Managed at Department | | | | |
| 44 | Direct Paid Faculty Salaries & Benefits | - | - | - | |
| 45 | *Faculty Salary & Benifit Allocations* | | | | |
| 46 | Faculty Salaries | 268,915 | 312,620 | (312,6) | |
| 47 | Faculty Benefits | 31,341 | 528,611 | 3,106,6 | |
| 48 | Nonfaculty Salaries | 664,809 | 139,689 | 277,9 | |
| 49 | Nonfaculty Benefits | 119,215 | 993,514 | 1,206,2 | |
| | | | 167,630 | 99,2 | |
| 50 | Subtotal | 1,084,280 | 2,142,065 | 4,377,3 | |
| 51 | Other Expenses | 634,510 | 633,144 | 509,7 | |
| 52 | ICR Returned | 196,435 | (196,435) | - | |
| 53 | NonCash Expenses | - | - | - | |
| 54 | UHC Database Adjustment | | | | |
| 55 | Subtotal | 830,945 | 436,708 | 509,7 | |
| 56 | Total Managed at Department | 1,915,225 | 2,578,773 | 4,887,0 | |
| | Other | | | | |
| 57 | Allocation of central services - Univ | 131,146 | 485,432 | - | |
| 58 | Allocation of central services - Health System | - | - | - | |
| 59 | Allocation of central services - Dean | 103,286 | 382,310 | - | |
| 60 | Other | - | - | - | |
| 61 | Subtotal | 234,433 | 867,742 | - | |
| 62 | Total Uses of Funds | 2,149,658 | 3,446,515 | 4,887,09 | |
| 63 | Total Sources Over/(Under) Uses of Funds | (0) | (108,312) | | |
| 64 | Use of Prior Period Reserves | | | | |
| 65 | Total Sources Over/(Under) Uses of Funds | $ (0) | $ (108,312) | $ | $ |

FIG. 15C

|  | | A | B | C | D |
|---|---|---|---|---|---|
|  | | School of Medicine | | Faculty Clinical Practice | Total |
|  | | Externally Funded Research | Other Academic | | |
| SOURCES OF FUNDS | | | | | |
| | *Funds Generated - External* | | | | |
| 1 | Net Patient Care Revenue | $ - | $ - | $ 5,446,758 | $ 5,446,758 |
| 2 | DER - Federal | 93,201 | - | - | 93,201 |
| 3 | DER - NonFederal   ICR - Federal | 54,670 | - | - | 54,670 |
| 4 | ICR - NonFederal | 36,814 | - | - | 36,814 |
| 5 | Tuition and Fees | 5,679 | - | - | 5,679 |
| 6 | Direct Paid Salaries | - | 343,554 | - | 343,554 |
| 7 | Other External Generated | - | - | - | - |
| 8 | *Subtotal* | - | - | - | - |
| 10 | Funds Generated - Internal | 190,364 | 343,554 | 5,446,758 | 5,980,676 |
|  | From the Hospital | | | | |
| 11 | Other | - | - | 779,980 | 779,980 |
| 12 | *From Hospital - Unreimbursed Expenses* | - | - | - | - |
| 13 | *Other - Unreimbursed Expenses* | - | 1,148,123 | - | 1,148,123 |
| 14 | *Subtotal* | - | - | - | - |
| 16 | Total Funds Generated | - | 1,148,123 | 779,980 | 1,928,103 |
| 17 | Funds Invested | 190,364 | 1,491,677 | 6,226,738 | 7,906,779 |
|  | Institutional Investment Funds Provided From University | | | | |
| 18 | From Health System | - | - | - | - |
| 19 | From Dean | - | - | - | - |
| 20 | Other | - | 1,697,562 | - | 1,697,562 |
| 21 | *Subtotal* | - | - | - | - |
| 22 | Expenses Incurred on Behalf of Dept | - | 1,697,562 | - | 1,697,562 |
|  | University | | | | |
| 23 | Health System | 93,170 | 125,111 | 343,286 | 561,567 |
| 24 | Dean | - | - | - | - |
| 25 | Other | 29,195 | 35,108 | 252,745 | 317,048 |
| 26 | *Subtotal* | - | - | - | - |
| 27 | | 122,365 | 160,219 | 596,031 | 878,615 |
|  | Funds Generated Retained Research/ICR Retained | | | | |
| 28 | Teaching | (56,274) | - | - | (56,274) |
| 29 | Clinical | - | (343,554) | - | (343,554) |
| 30 | *Subtotal* | - | - | (456,670) | (456,670) |
| 31 | | (56,274) | (343,554) | (456,670) | (856,498) |

FIG. 16A

| | | A | B | C | D |
|---|---|---|---|---|---|
| | | School of Medicine | | Faculty Clinical Practice | Total |
| | | Externally Funded Research | Other Academic | | |
| | Support Between AMC Operating Units | | | | |
| 32 | From Hospital | $ - | $ - | $ 187,410 | $ 187,410 |
| 33 | Other | - | - | - | - |
| 34 | *From Hospital - Unreimbursed Expense* | - | (1,148,123) | - | (1,148,123) |
| 35 | *Other - Unreimbursed Expense* | - | - | - | - |
| 37 | Subtotal | - | (1,148,123) | 187,410 | (960,713) |
| | Departmental Investment | | | | |
| 38 | Across Missions | - | - | - | - |
| 39 | *Across Missions - Unreimbursed Expense* | - | 684,714 | (684,714) | - |
| 40 | Other | - | 127,510 | - | 127,510 |
| 41 | Subtotal | - | 812,224 | (684,714) | 127,510 |
| 42 | Total Funds Invested | 66,091 | 1,178,328 | (357,943) | 886,476 |
| 43 | Total Sources of Funds | 256,455 | 2,670,005 | 5,868,795 | 8,795,255 |
| USES OF FUNDS | | | | | |
| | Managed at Department | | | | |
| 44 | Direct Paid Faculty Salaries & Benefits | - | - | 967,390 | 967,390 |
| 45 | Faculty Salary & Benefit Allocations | - | 684,714 | (684,714) | - |
| 46 | Faculty Salaries | 66,756 | 1,487,846 | 1,924,262 | 3,478,864 |
| 47 | Faculty Benefits | 11,665 | 267,813 | 331,949 | 611,427 |
| 48 | Nonfaculty Salaries | 27,390 | 1,245 | 153,958 | 182,593 |
| 49 | Nonfaculty Benefits | 4,837 | 224 | 26,559 | 31,620 |
| 50 | Subtotal | 110,648 | 2,441,842 | 2,719,404 | 5,271,894 |
| 51 | Other Expenses | 23,438 | 66,909 | 3,155,657 | 3,246,004 |
| 52 | ICR Returned | - | - | - | - |
| 53 | NonCash Expenses | - | - | - | - |
| 55 | Subtotal | 23,438 | 66,909 | 3,155,657 | 3,246,004 |
| 56 | Total Managed at Department | 134,086 | 2,508,751 | 5,875,061 | 8,517,898 |
| | Other | | | | |
| 57 | Allocation of Central Services - Univ | 93,170 | 125,111 | 343,286 | 561,567 |
| 58 | Allocation of Central Services - Health System | - | - | - | - |
| 59 | Allocation of Central Services - Dean | 29,195 | 35,108 | 252,745 | 317,048 |
| 60 | Other | - | - | - | - |
| 61 | Subtotal | 122,365 | 160,219 | 596,031 | 878,615 |
| 62 | Total Uses of Funds | 256,451 | 2,668,970 | 6,471,092 | 9,396,513 |
| 65 | Total Sources Over/(Under) Uses of Funds | $ 4 | $ 1,035 | $ (602,297) | $ (601,258) |

FIG. 16B

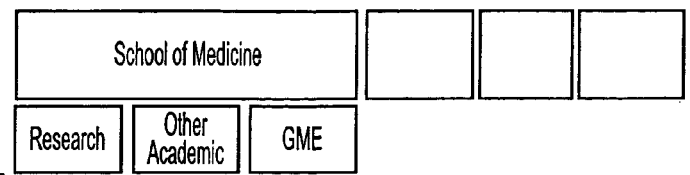

FIG. 17A

| | Research | Other Academic | GME | School of Medicine | | Total |
|---|---|---|---|---|---|---|
| SOURCES OF FUNDS | | | | | | |
| Funds Generated | | | | | | |
| 1 Net Patient Care Revenue | | | | 5,446,758 | - | 5,446,758 |
| 2 DER - Federal | 93,201 | | | | | 93,201 |
| 3 DER - NonFederal | 54,670 | | | | | 54,670 |
| 4 ICR - Federal | 36,814 | | | | | 36,814 |
| 5 ICR - NonFederal | 5,679 | | | | | 5,679 |
| 6 Allocation of Tuition and Fees | | 343,554 | | | | 343,554 |
| 7 Direct Paid Salaries | | | | | | - |
| 8 Other Generated | - | | | | | - |
| Total | 190,364 | 343,554 | - | 5,446,758 | - | 5,980,676 |
| Purchased Services | | | | | | |
| 12 From the FPP | | | | | | - |
| 12 From the SOM | | | | | | - |
| 11 From the Hospital | | | | 779,980 | | 779,980 |
| 13 From the Hospital - Unreimbursed | | | 1,148,123 | - | | 1,148,123 |
| 12 From the Univ/VPHA | | | | | | - |
| Total | - | - | 1,148,123 | 779,980 | - | 1,928,103 |
| Total Funds Generated | 190,364 | 343,554 | 1,148,123 | 6,226,738 | - | 7,908,779 |
| Funds Invested | | | | | | |
| Institutional Investment | | | | | | |
| 20 State General Funds | | 1,435,906 | | | | 1,435,906 |
| 20 State Benefits Payments | - | 261,656 | | | | 261,656 |
| Unreimbur Expenses Incurred on Behalf Depts | | | | | | - |
| 25 Allocation of Central Services - Dean | 29,195 | 35,108 | | 252,745 | | 317,048 |
| 23 Allocation of Central Services - Univ/VPHA | 93,170 | 125,111 | | 343,286 | | 561,566 |
| Subtotal | 122,364 | 160,219 | - | 596,031 | - | 878,614 |
| Funds Generated Retained by Institution | | | | | | |
| 28 Research/ICR Retained | (56,274) | | | | | (56,274) |
| 29 Teaching | | (343,554) | | | | (343,554) |
| 30 Clinical | | | | (456,670) | | (456,670) |
| Subtotal | (56,274) | (343,554) | - | (456,670) | - | (856,498) |
| Other Support | | | | | | |
| 38 By the FPP | 544,541 | | 140,172 | (684,714) | | - |
| 38 By the SOM | | | 1,007,950 | | | - |
| 32 By the Hospital | | (1,007,950) | | 187,410 | - | 187,410 |
| 34 By the Hospital - Unreimbursed | | | (1,148,123) | - | | (1,148,123) |
| 32 By the Strategic Investment Fund | | | | - | | - |
| 33 By the Univ/VPHA | | | | | | - |
| Subtotal | 544,541 | (1,007,950) | - | (497,304) | - | (960,713) |
| Departmental Investment | | | | | | |
| 40 Endowment Utilized | | | | | | - |
| 40 Gifts/Transfers from Reserves | | 127,510 | | | | 127,510 |
| Subtotal | - | 127,510 | - | - | - | 127,510 |

FIG. 17B

| | | School of Medicine | | | | |
|---|---|---|---|---|---|---|
| | | Research | Other Academic | GME | | |
| | Total Funds Invested | 610,632 | 633,787 | - | (357,943) | - | 886,476 |
| | Total Sources of Funds | 800,996 | 977,340 | 1,148,123 | 5,868,795 | - | 8,795,254 |

| USES OF FUNDS | | | | | | |
|---|---|---|---|---|---|---|
| Paid at Department | | | | | | |
| 46 | Faculty Salaries | 66,756 | 1,487,846 | | 1,924,262 | | 3,478,864 |
| 44 | Faculty Salaries, Direct Paid/SIF | | | | 819,822 | | 819,822 |
| 45 | Faculty Salaries, Non-realized | 461,476 | (854,195) | 972,985 | (580,266) | | - |
| 48 | Nonfaculty Salaries | 27,390 | 1,245 | | 153,958 | - | 182,593 |
| 47 | Faculty Benefits | 11,665 | 6,375 | | 331,949 | | 349,989 |
| 47 | Faculty Benefits, State Paid | | 261,438 | | | | 261,438 |
| 44 | Faculty Benefits, Direct Paid/SIF | - | | | 147,568 | | 147,568 |
| 48 | Faculty Benefits, Non-realized | 83,066 | (153,755) | 175,137 | (104,448) | | - |
| 49 | Nonfaculty Benefits | 4,837 | 5 | | 26,559 | | 31,401 |
| 49 | Nonfaculty Benefits, State Paid | | 219 | | | - | 219 |
| 51 | Equipment | 16,736 | 9,530 | | 27,658 | | 53,924 |
| 51 | Supplies | 1,799 | 27,950 | | 84,574 | | 114,323 |
| 51 | Space/Rent | - | - | | - | | - |
| 51 | Housekeeping | - | - | | - | | - |
| 51 | Utilities | - | - | | - | | - |
| 51 | Security | - | - | | - | | - |
| 51 | Library | - | - | | - | | - |
| 51 | Malpractice Insurance | - | - | | 286,982 | | 286,982 |
| 51 | Other | 4,903 | 29,429 | | 2,738,601 | - | 2,772,939 |
| 51 | Other SIF | | | | | | - |
| 51 | Admin Unit | | | | 17,836 | - | 17,836 |
| 51 | Expense Adjustment | - | - | | | | - |
| | Subtotal | 678,627 | 816,086 | 1,148,123 | 5,875,061 | - | 8,517,897 |
| | Less Purchased Services | - | - | - | - | - | - |
| | Internally Purchased Services | | | | | | |
| |   To the FPP | | | | | | - |
| |   To the SOM | | | | | | - |
| |   To the Hospital | | | | | | - |
| |   To the Univ/VPHA and subs | | | | | | - |
| | Subtotal | - | - | - | - | - | - |
| | Subtotal Paid at Dept | 678,627 | 816,086 | 1,148,123 | 5,875,061 | - | 8,517,897 |
| Paid Centrally | | | | | | | |
| 59 | Allocation of Central Services - Dean | 29,195 | 35,108 | | 252,745 | - | 317,048 |
| 57 | Allocation of Central Services - Univ/VPHA | 93,170 | 125,111 | | 343,286 | | 561,566 |
| | Subtotal Paid Centrally | 122,364 | 160,219 | - | 596,031 | | 878,614 |
| | Total Uses of Funds | 800,992 | 976,304 | 1,148,123 | 6,471,092 | - | 9,396,511 |
| | Total Sources Over (Under) Uses of Funds | 4 | 1,036 | - | (602,297) | - | (601,257) |

| Clinical Department Ratios - UIC Health Sciences Center | | | | | | | | |
|---|---|---|---|---|---|---|---|---|
| | Anesthesiology | Dermatology | Emergency Medicine | Family Medicine | TOTAL Medicine | Neurology | OB/GYN | Opthalmology |

Key Ratios - SOM and FPP

Data Elements

| | Anesthesiology | Dermatology | Emergency Medicine | Family Medicine | TOTAL Medicine | Neurology | OB/GYN | Opthalmology |
|---|---|---|---|---|---|---|---|---|
| Faculty Salaries & Benefits Reset | 684,714 | (245,471) | 243,140 | (1,083,385) | 918,220 | (10,991) | 558,961 | 273,845 |
| Faculty Salaries & Benefits Paid With Research Dollars | 78,421 | 166,999 | 214,053 | 237,777 | 3,857,299 | 265,235 | 589,209 | 1,491,270 |
| Direct Paid Salaries | | | | | | | | |
| · Research | - | - | - | - | - | - | - | - |
| · Teaching | - | - | - | - | 931,991 | - | - | - |
| · Clinical | 967,390 | 53,035 | 1,334,796 | 61,676 | 1,378,786 | 201,813 | 649,818 | 25,743 |
| Funds Generated Retained | | | | | | | | |
| · Research | (56,274) | (40,754) | (33,790) | (17,663) | (856,067) | (95,279) | (165,269) | (769,993) |
| · Teaching | (343,554) | (37,485) | (415,207) | (167,103) | (521,354) | (94,350) | (395,127) | (197,936) |
| · Clinical | (456,670) | (64,204) | - | (67,736) | (708,158) | (87,696) | (447,924) | (361,472) |
| Internal Funds Generated From the Hospital | - | 92,024 | 215,979 | 252,607 | 1,484,913 | 213,517 | 742,915 | 948,708 |
| Int. Funds Gen. From the Hosp.- Unreimb. Exp.- Teaching | 1,148,123 | 226,625 | - | 864 | 89,675 | 155,168 | - | 330,617 |
| Internal Funds Generated From the Hosp.- Unreimb. Exp.- Clin | | | | | | | | |

FIG. 18A

| Clinical Department Ratios - UIC | | | | | | | | | |
|---|---|---|---|---|---|---|---|---|---|
| | Pathology | TOTAL Peds | Physical Medicine | Preventive Medicine | Psychiatry | Radiation Oncology | Radiology | TOTAL Surgery | TOTAL Clinical |

Key Ratios - SOM and FPP

Data Elements

| | Pathology | TOTAL Peds | Physical Medicine | Preventive Medicine | Psychiatry | Radiation Oncology | Radiology | TOTAL Surgery | TOTAL Clinical |
|---|---|---|---|---|---|---|---|---|---|
| Faculty Salaries & Benefits Reset | (106,356) | 21,668 | 106,258 | - | (2,196,360) | - | 336,914 | 2,107,050 | 1,608,207 |
| Faculty Salaries & Benefits Paid With Research Dollars | 56,480 | 847,971 | 1,531 | - | 7,189,485 | - | - | 990,624 | 15,986,354 |
| Direct Paid Salaries | | | | | | | | | |
| · Research | - | - | - | - | - | - | - | 82,242 | 1,014,234 |
| · Teaching | - | - | - | - | 257,771 | - | - | 2,254,205 | 9,733,967 |
| · Clinical | 1,651,522 | 468,742 | 152,279 | - | - | - | 276,391 | | |
| Funds Generated Retained | | | | | | | | | |
| · Research | (52,305) | (549,597) | - | - | (1,034,670) | - | (11,063) | (273,550) | (3,956,274) |
| · Teaching | (255,049) | (423,070) | (86,863) | - | (844,753) | - | (96,413) | (661,167) | (4,539,431) |
| · Clinical | (98,208) | (478,949) | (31,298) | - | (153,697) | - | (505,688) | (1,022,092) | (4,483,792) |
| Internal Funds Generated From the Hospital | - | - | - | - | - | - | - | - | - |
| Int. Funds Gen. From the Hosp - Unreimb. Exp. - Teaching | 339,144 | 1,226,133 | 147,224 | - | 1,226,563 | - | 654,770 | 2,039,564 | 10,732,185 |
| Internal Funds Generated From the Hosp - Unreimb. Exp. - Clin | - | 303,638 | - | - | - | - | 337,209 | 573,578 | 2,017,373 |

FIG. 18B

Clinical Department Ratios - UIC Health Sciences Center

| Key Ratios - SOM and FPP | Anesthesiology | Dermatology | Emergency Medicine | Family Medicine | TOTAL Medicine | Neurology | OB/GYN | Opthalmology |
|---|---|---|---|---|---|---|---|---|
| External FG/FTE | $ 436,865 | $ 140,944 | $ 414,244 | $ 323,622 | $ 350,668 | $ 234,376 | $ 352,885 | $ 356,187 |
| Internal FG/FTE | 56,974 | 31,247 | 11,891 | 4,738 | 17,769 | 36,373 | 10,647 | 13,463 |
| Total FG/FTE | $ 493,839 | $ 172,191 | $ 426,136 | $ 328,360 | $ 368,437 | $ 270,749 | $ 363,532 | $ 369,650 |
| Clinical Ext FG/FTE | $ 397,864 | $ 101,267 | $ 344,593 | $ 84,496 | $ 217,079 | $ 163,805 | $ 270,369 | $ 209,876 |
| Research Ext FG/FTE | 13,905 | 35,054 | 33,894 | 24,917 | 119,476 | 56,696 | 61,023 | 128,670 |
| Total Exp as a % of Ext FG | 157.1% | 213.0% | 123.4% | 139.9% | 164.0% | 171.0% | 162.6% | 125.7% |
| Total Fac.Sal + Ben as a % of Ext FG | 84.6% | 93.7% | 50.2% | 52.7% | 75.3% | 85.8% | 77.3% | 56.3% |
| Clin Non-Fac.Sal + Ben (People) as a % of Clin Ext F | 3.3% | 56.1% | 0.1% | 60.6% | 28.5% | 38.8% | 40.6% | 44.0% |
| Clin Non-Fac.Sal + Ben (Other) as a % of Clin Ext FG | 57.9% | 63.9% | 55.9% | 54.4% | 46.3% | 44.3% | 39.2% | 27.5% |
| Total Fac.Sal + Ben per FTE | $ 369,443 | $ 132,002 | $ 208,016 | $ 170,596 | $ 264,223 | $ 201,126 | $ 272,827 | $ 200,419 |
| Total Non-Fac.Sal + Ben (People) per FTE | 15,647 | 69,056 | 34,742 | 134,294 | 90,238 | 76,938 | 123,883 | 107,445 |
| Total Non-Fac.Sal + Ben (Other) per FTE | 301,287 | 99,138 | 268,381 | 147,989 | 220,769 | 122,787 | 177,256 | 139,757 |
| Total Exp per FTE | $ 686,378 | $ 300,196 | $ 511,139 | $ 452,879 | $ 575,229 | $ 400,851 | $ 573,966 | $ 447,622 |
| Actual FU/FTE | $ 148,619 | $ 145,064 | $ 130,043 | $ 181,030 | $ 199,709 | $ 139,223 | $ 157,804 | $ 109,710 |
| Dept FG/FTE | 9,314 | 513 | 457 | 4 | 9,844 | 3,900 | 282 | 7,974 |
| Net CPS/FTE | 64,179 | 25,818 | 54,693 | 49,122 | 61,526 | 38,201 | 48,047 | 40,104 |
| Number of FTE | 14 | 9 | 12 | 13 | 62 | 8 | 27 | 26 |
| Number of MD | . | . | . | . | . | . | . | . |
| Faculty Salaries | | | | | | | | |
| Clinical External Funds Generated as a % of Total Ext | 91.1% | 71.8% | 83.2% | 26.1% | 61.9% | 69.9% | 76.6% | 58.9% |
| Clinical Fac.Sal. & Ben. as a % of Clinical Ext. Fund | 46.6% | 57.8% | 38.3% | 119.4% | 46.8% | 54.7% | 63.4% | 32.4% |
| Clinical Fac.Sal. & Ben. as a % of Total Fac. Sal. & Ben. | | | | | | | | |
| • with salary reset | 50% | 44% | 63% | 59% | 38% | 45% | 63% | 34% |
| • without salary reset | 64% | 24% | 73% | 11% | 44% | 44% | 71% | 39% |
| Clinical Margin as a % of Total Margin | 100% | 100% | 252% | 81% | 114% | 98% | 101% | 96% |

FIG. 18C

Clinical Department Ratios - UIC Health Sciences Center

| | Pathology | TOTAL Peds | Physical Medicine | Preventative Medicine | Psychiatry | Radiation Oncology | Radiology | TOTAL Surgery | TOTAL Clinical |
|---|---|---|---|---|---|---|---|---|---|
| Key Ratios - SOM and FPP | | | | | | | | | |
| External FG/FTE | $ 179,823 | $ 211,170 | $ 118,018 | - | $ 323,737 | - | $ 371,378 | $ 404,670 | $ 324,248 |
| Internal FG/FTE | 23,512 | 16,004 | 24,567 | - | 4,358 | - | 33,457 | 30,204 | 18,900 |
| Total FG/FTE | $ 203,335 | $ 227,174 | $ 142,585 | - | $ 328,095 | - | $ 404,835 | $ 434,874 | $ 343,148 |
| Clinical Ext FG/FTE | $ 140,779 | $ 130,369 | $ 100,213 | - | $ 38,215 | - | $ 361,302 | $ 348,879 | $ 202,928 |
| Research Ext FG/FTE | 16,854 | 56,504 | 417 | - | 238,391 | - | 3,981 | 39,950 | 91,344 |
| Total Exp as a % of Ext FG | 232.1% | 142.3% | 270.1% | 0.0% | 145.3% | 0.0% | 122.7% | 150.9% | 151.2% |
| Total Fac Sal + Ben as a % of Ext FG | 158.9% | 86.6% | 135.4% | 0.0% | 69.7% | 0.0% | 74.1% | 74.9% | 74.9% |
| Clin Non Fac Sal + Ben (People) as a % of Clin Ext F | 2.7% | 3.8% | 52.0% | 0.0% | 48.0% | 0.0% | 0.9% | 22.4% | 22.7% |
| Clin Non Fac Sal + Ben (Other) as a % of Clin Ext FG | 36.3% | 34.1% | 49.7% | 0.0% | 45.6% | 0.0% | 36.4% | 36.4% | 41.5% |
| Total Fac Sal + Ben per FTE | $ 285,683 | $ 182,951 | $ 159,740 | - | $ 225,785 | - | $ 275,033 | $ 302,992 | $ 242,728 |
| Total Non Fac Sal + Ben (People) per FTE | 26,289 | 19,094 | 60,455 | - | 71,671 | - | 6,564 | 97,293 | 72,200 |
| Total Non Fac Sal + Ben (Other) per FTE | 105,449 | 98,358 | 98,547 | - | 172,976 | - | 174,263 | 210,550 | 175,332 |
| Total Exp per FTE | $ 417,421 | $ 300,404 | $ 318,742 | - | $ 470,432 | - | $ 455,860 | $ 610,836 | $ 490,259 |
| Actual FI/FTE | $ 253,052 | $ 83,806 | $ 125,056 | - | $ 133,218 | - | $ 45,521 | $ 192,484 | $ 149,162 |
| Dept FI/FTE | 4,682 | 1,292 | 230 | - | 2,580 | - | 177 | 15,761 | 5,648 |
| Net CPS/FTE | 45,677 | 29,659 | 29,226 | - | 62,137 | - | 41,902 | 57,248 | 50,433 |
| Number of FTE | 13 | 44 | 6 | - | 58 | - | 18 | 48 | 358 |
| Number of MD | - | - | - | - | - | - | - | - | - |
| Faculty Salaries | | | | | | | | | |
| Clinical External Funds Generated as a % of Total Ext | 78.3% | 61.7% | 84.9% | 0.0% | 11.8% | 0.0% | 97.3% | 86.2% | 62.6% |
| Clinical Fac. Sal. & Ben. as a % of Clinical Ext. Fund | 122.2% | 73.4% | 69.9% | 0.0% | 155.6% | 0.0% | 55.8% | 45.6% | 56.4% |
| Clinical Fac. Sal. & Ben. as a % of Total Fac. Sal. & Ben. | | | | | | | | | |
| • with salary reset | 60% | 52% | 44% | 0% | 26% | 0% | 73% | 52% | 47% |
| • without salary reset | 57% | 53% | 55% | 0% | 10% | 0% | 80% | 67% | 49% |
| Clinical Margin as a % of Total Margin | 97% | 101% | 87% | 0% | 78% | 0% | 104% | 99% | 192% |

KEY DEPARTMENT RATIOS - UHC BENCHMARKS - FY 1997
ANESTHESIOLOGY

| | A | B | C | D | E | F | G | H | I | J | K | L | Mean | Standard Deviation |
|---|---|---|---|---|---|---|---|---|---|---|---|---|---|---|
| ...tated per Faculty FTE | $ 340,822 | $ 248,561 | $ 436,865 | $ 272,085 | $ 234,341 | $ 186,707 | $ 259,298 | $ 312,503 | $ 397,155 | $ 164,572 | $ 312,177 | $ 341,409 | $ 292,208 | $ 80,714 |
| ...ated per Faculty FTE | 6,524 | 47,662 | 56,974 | 14,152 | - | 19,776 | 40,937 | 5,266 | 10,481 | - | - | 56,499 | 21,523 | 22,560 |
| ...ed per Faculty FTE | 347,346 | 296,223 | 493,839 | 286,237 | 234,341 | 206,483 | 300,235 | 317,769 | 407,636 | 164,572 | 312,177 | 397,908 | 313,731 | 90,849 |
| als Generated per Faculty FTE | 231,243 | 246,877 | 397,864 | 239,580 | 230,765 | 165,182 | 244,919 | 304,315 | 320,962 | 142,847 | 289,006 | 337,508 | 262,589 | 71,775 |
| ands Generated per Faculty FTE | 93,835 | 30 | 13,905 | 25,350 | 792 | 17,833 | 10,436 | 106 | 72,249 | 19,177 | 19,141 | 602 | 22,788 | 29,815 |
| Percent of External Funds Generated | 123.0% | 122.2% | 157.1% | 115.4% | 190.9% | 144.3% | 135.2% | 105.0% | 108.5% | 195.7% | 110.6% | 115.4% | 115.3% | 31.1% |
| nsation as a Percent of External Funds Generated | 51.1% | 67.0% | 84.6% | 75.6% | 85.8% | 94.8% | 68.6% | 54.6% | 56.3% | 107.4% | 51.4% | 62.1% | 71.6% | 18.3% |
| Compensation as a Percent of Clinical Generated | 22.6% | 37.9% | 3.3% | 7.3% | 39.7% | 9.7% | 23.4% | 13.3% | 12.0% | 3.2% | 10.6% | 12.8% | 16.3% | 12.2% |
| Noncompensation Expense as a Percent at Funds Generated | 8.8% | 9.5% | 57.9% | 18.1% | 21.6% | 21.5% | 27.6% | 27.2% | 29.5% | 9.1% | -1.9% | 39.7% | 22.4% | 16.0% |
| ...ensation per Faculty FTE | $ 174,126 | $ 166,552 | $ 369,443 | $ 205,587 | $ 200,963 | $ 176,970 | $ 177,901 | $ 170,630 | $ 223,520 | $ 176,716 | $ 160,525 | $ 211,922 | $ 201,246 | $ 56,555 |
| Compensation per Faculty FTE | $ 130,023 | $ 100,845 | $ 15,647 | $ 21,623 | $ 96,667 | $ 20,976 | $ 65,803 | $ 46,116 | $ 85,126 | $ 36,621 | $ 47,387 | $ 45,365 | $ 59,350 | $ 36,496 |
| Compensation Expense per Faculty FTE | 115,182 | 36,181 | 301,287 | 86,863 | 149,698 | 71,529 | 106,852 | 111,377 | 122,141 | 108,723 | 105,542 | 136,535 | 120,993 | 64,026 |
| Faculty FTE | 419,331 | 303,678 | 686,377 | 314,073 | 447,328 | 269,475 | 350,556 | 328,123 | 430,787 | 322,060 | 313,454 | 393,822 | 381,589 | 111,363 |

FIG. 19B-1

| KEY DEPARTMENT RATIOS - UHC BENCHMARKS - FY 1997 | | | | | | | | | | | | | Mean | Standard Deviation |
|---|---|---|---|---|---|---|---|---|---|---|---|---|---|---|
| ANESTHESIOLOGY | | | | | | | | | | | | | | |
| | A | B | C | D | E | F | G | H | I | J | K | L | | |
| ed per Faculty FTE | $ 67,652 | $ 27,660 | $148,619 | $ 17,780 | $158,051 | $ 73,019 | $ 42,832 | $ 20,826 | $ 40,470 | $157,482 | $ 57,023 | $ 16,077 | $ 68,961 | $ 54,949 |
| Invested per Faculty FTE | $ 6,275 | $ 4,061 | $ 9,314 | $ 5,569 | $ 237 | $ 4,827 | $ 12 | $ 157 | $ 15,519 | $ 3,178 | $ 1,642 | $ 20,756 | $ 5,962 | $ 6,431 |
| Service per Faculty FTE | $ 44,087 | $ 17,092 | $ 64,179 | $ 32,418 | $ 98,160 | $ 33,089 | $ 37,322 | $ 17,012 | $ 22,342 | $ 73,462 | $ 39,044 | $ - | $ 39,851 | $ 27,273 |
| FTEs | 25.0 | 57.0 | 13.7 | 36.6 | 21.9 | 47.2 | 53.3 | 32.0 | 43.4 | 67.0 | 51.8 | 40.0 | 40.7 | 15.7 |
| | 0.0 | 0.0 | 0.0 | 33.0 | 0.0 | 0.0 | 0.0 | 0.0 | 0.0 | 0.0 | 0.0 | 0.0 | 2.8 | 9.5 |
| ds Generated as a Percent of Total Generated | 67.8% | 99.3% | 91.1% | 88.1% | 98.5% | 88.5% | 94.5% | 97.4% | 80.8% | 86.8% | 92.6% | 98.9% | 90.4% | 9.1% |
| Compensation as a Percent of Clinical Generated | 53.1% | 53.0% | 46.6% | 75.9% | 76.3% | 37.0% | 62.0% | 42.3% | 55.3% | 71.0% | 43.6% | 62.5% | 56.6% | 13.2% |
| Compensation as a Percent of Total Faculty Reset | 70.6% | 78.6% | 50.2% | 88.4% | 87.7% | 34.5% | 65.4% | 75.4% | 79.4% | 57.4% | 78.6% | 99.5% | 71.8% | 18.2% |
| y reset | 77.8% | 82.4% | 63.7% | 88.4% | 92.5% | 69.4% | 89.3% | 80.5% | 79.4% | 57.4% | 78.6% | 99.5% | 79.9% | 12.0% |
| gin as a Percent of Total Operating Margin | 0.0% | 112.5% | 100.2% | 100.0% | 100.1% | 86.7% | 100.0% | 176.9% | 111.5% | 50.0% | 100.0% | 83.6% | 91.5% | 41.2% |

FIG. 19B-2

FUNDS FLOW SYSTEM FOR ACADEMIC HEALTH CENTERS

CROSS-REFERENCE TO RELATED APPLICATIONS

This application claims priority from U.S. Provisional Application No. 60/162,328, filed Oct. 29, 1999, which is incorporated herein by reference in its entirety.

FIELD OF THE INVENTION

The invention relates to a system and method for tracking and reporting the flow of funds and more particularly to a system and method for tracking and reporting the flow of funds between participants in an academic health center comprising a school of medicine, a hospital and a faculty clinical practice, thus allowing comparisons between the different participants and departments of participants and comparisons among different academic health centers.

BACKGROUND OF THE INVENTION

FIG. 1 is a block diagram of an academic health center (AHC) or an academic clinical enterprise having as participants a school of medicine 12, a hospital 14 and a faculty practice plan 16. The AHC 10 allows for the advancement of medical knowledge, providing medical care to patients and preparing medical students. The AHC 10 allows each participant to perform their given tasks with support from the other participants. For example, since a school of medicine 12 can only provide a limited education to its students, the students must rely on the doctors and hospital 14 to provide real life training.

Although each participant in an AHC interacts with and relies on the other participants, there is no proper method to account for and determine the value of these partnerships and relationships in monetary measures. Without proper accounting, the participants cannot properly compare the cost and benefits each receives as part of the AHC 10. Similarly, it is difficult to compare the efficiency of a department within a participant. For example, a hospital cannot measure the efficiency of its orthopedics department with the ophthalmology department. Without proper accounting, a hospital cannot compare the efficiency of its orthopedics department with other orthopedic departments located at different hospitals in other AHC's.

One of the reasons for such problems is that each participant has its own accounting system thus each participant treats costs differently. Moreover, even if the participants use the same accounting system, the participants still cannot make realistic comparisons because the participants do not typically define transactions and measures in the same manner, nor do they account for hidden costs or income such as service and benefits which they receive for free from another participant. Without a shared accounting system which properly accounts for each transaction, whether it is a cash or non-cash transaction, the participants cannot use meaningful benchmarking procedures to determine how a department within a participant or a participant is operating.

SUMMARY OF THE INVENTION

The problems of the prior art overcome in accordance with one embodiment of the invention by identifying, pricing, and categorizing each transaction between the parties thereby allowing the costs and values of the services between each party to be analyzed and appropriate action can be taken to correct for any imbalance in costs or benefits that a participant receives at the cost of another participant.

The present invention provides both processes and comparative financial data that enable the participants of an AHC: the hospital, practice plan and school of medicine, which are referred to as the participants in the "triangle," to use common definitions and formats to identify and discuss the real costs and value of the services each participant provides and how services are funded. The invention permits all participants start from common ground with common definitions. The present invention also provides departmental analyses of sources and uses of funds, i.e., income statements, which allow evaluation of departmental performance in a mission-based format. Thus the present invention provides for analyses of the following: academic medical center interdependencies; productivity, efficiency and operating performance across missions; investment of academic center resources; net state and community support; and benchmarking. In addition, because the format logic and definitions have been standardized for all participants, comparison across institutions and departments is possible.

On one level, benchmarking allows one participant in an AHC to determine how that participant compares with other participants in other AHCs, e.g., hospital A verse hospital B and/or hospital C. Benchmarking can also be used to compare one department within a participant with another department within the same participant, e.g., pediatrics verse cardiovascular. Benchmarking also allows for a department in one participant to be compared with the same department in another participant in another AHC, e.g., pediatrics in hospital A verse pediatrics in hospital B. Such comparisons are possible if each party is being compared using the same framework. In other words, for one department to be compared to another department, the departments must categorize their costs in the same manner as well provide the same value for similar tasks. For example, if a first pediatrics group does not calculate the costs for bedsheets in their operating costs, but a second pediatrics group does, the two departments cannot be properly compared. Thus, there is a need for each party to label or categorize similar costs in similar ways.

Therefore, the participants in the system must identify and categorize their costs and services in the same manner thereby allowing for proper comparisons. Such comparisons will enable a party to determine if their costs are different from another party's costs for the same service and appropriate action can be taken. In order to do this, each participant needs to identify all transactions occurring between itself and the other participants, as well as transactions between itself and other relevant entities. For example, the school of medicine 12 needs to identify the transactions between the school of medicine 12 and the hospital 14 and care providers, as well as between the school of medicine 12 and the parent university, state, etc. All sources and uses of funds also need to be identified. Once identified, the sources and funds can be categorized using the same categories for each participant.

By analyzing the "commerce" or flow of funds between the participants in an AHC, departmental sources and uses of funds statements are prepared. The analyses need to be done such that the participants can understand and explain these transactions. Once all of the transactions have been identified and categorized, standard reports are generated. These reports can include a standard triangle statement and standard department statements, discussed hereinafter. The reports form the basis of a comparative database and are used to develop departmental ratios for comparison purposes.

The advantages of the present invention will become readily apparent to those skilled in the art from the following detailed description, wherein only the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE FIGURES

FIG. 6 is a chart of the transactions occurring in FIGS. 4 and 5.

FIG. 7 is a table of the internal commerce among the school of medicine, the faculty clinical practice and the hospital.

FIG. 8 is a table of the internal commerce among the school of medicine, the faculty clinical practice, the hospital, and the university, VPHA, health system, and state, county and community.

FIG. 10A is a chart of the transactions for programs and services illustrated in FIG. 9.

FIG. 10B is a chart of the transactions for OVCHS and Strategic Investment Fund as illustrated in FIG. 9.

FIG. 10C is a chart of the transactions for public aid and prison population illustrated in FIG. 9.

FIG. 10D is a chart of the transactions for research and training illustrated in FIG. 9.

FIG. 10E is a chart of the transactions for centrally provided services illustrated in FIG. 9.

FIG. 11 is a table of the purchased services and support by the hospital.

FIGS. 12A–B are tables of the strategic investment fund.

FIG. 13 is a listing of the different reporting departments.

FIGS. 15A–B are tables listing the sources of funds for the participants of the AHC.

FIG. 15C is a table listing the uses of funds for the participants of the AHC.

FIG. 16 is an exemplary standard departmental statement.

FIG. 17 is an exemplary customized departmental statement.

FIGS. 18A–D are exemplary tables of the clinical department ratios.

FIGS. 19A–B are exemplary tables of the key department ratios.

DESCRIPTION OF THE PREFERRED EMBODIMENT

The description of the invention which follows is exemplary. However, it should be clearly understood that the present invention may be practiced without the specific details described herein. Well known structures and devices are shown in block diagram form to avoid any unnecessarily obscuring the present invention.

An underpinning of the present invention is the recognition that AHCs are continually providing support to underfunded programs and making investments in new program and project development. The distinction between support and investments is often unclear. Even when an equity transfer is identified as an investment, expected returns, whether they be financial, programmatic or academic, are often poorly defined, if at all. One of the key benefits of the investment approach, i.e., viewing support as investments, is to prompt the equity provider and recipient to define the expected return.

Sources of investment equity, relatively common to all participants, include centrally retained indirect cost recovery from research, tuition and fees, taxes on clinical revenues, plant funds, trust fund earnings and internally restricted balances, current fund cash balances, net income and state and local appropriations when available. Uses of investment capital include funding of new programs and services, such as centers of excellence, construction projects, faculty additions, and primary care network development.

Many other equity transfers occur within AHCs, clearly of a support nature. In addition, support may take the form of unreimbursed expenses incurred by one party for the benefit of another. A major benefit of identifying the rationalizing equity transfers and other forms of support is that when continuing investment or support transfers makes no sense, the equity identified is essentially new strategic capital that can be direct to other uses.

Each participant is different, with its unique history, ownership, governance and financial relationships. Yet each participant wishes to compare itself to the other participants and to a common database in order to understand how others are addressing like issues and in order to benchmark productivity and efficiency.

Figure 1:
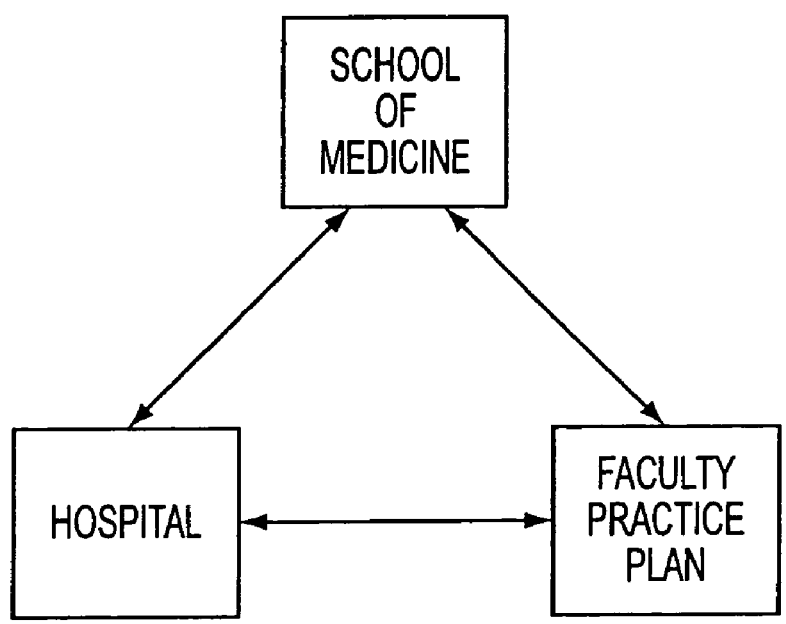
FIG. 1 is a block diagram of an academic health center.
Figure 2:
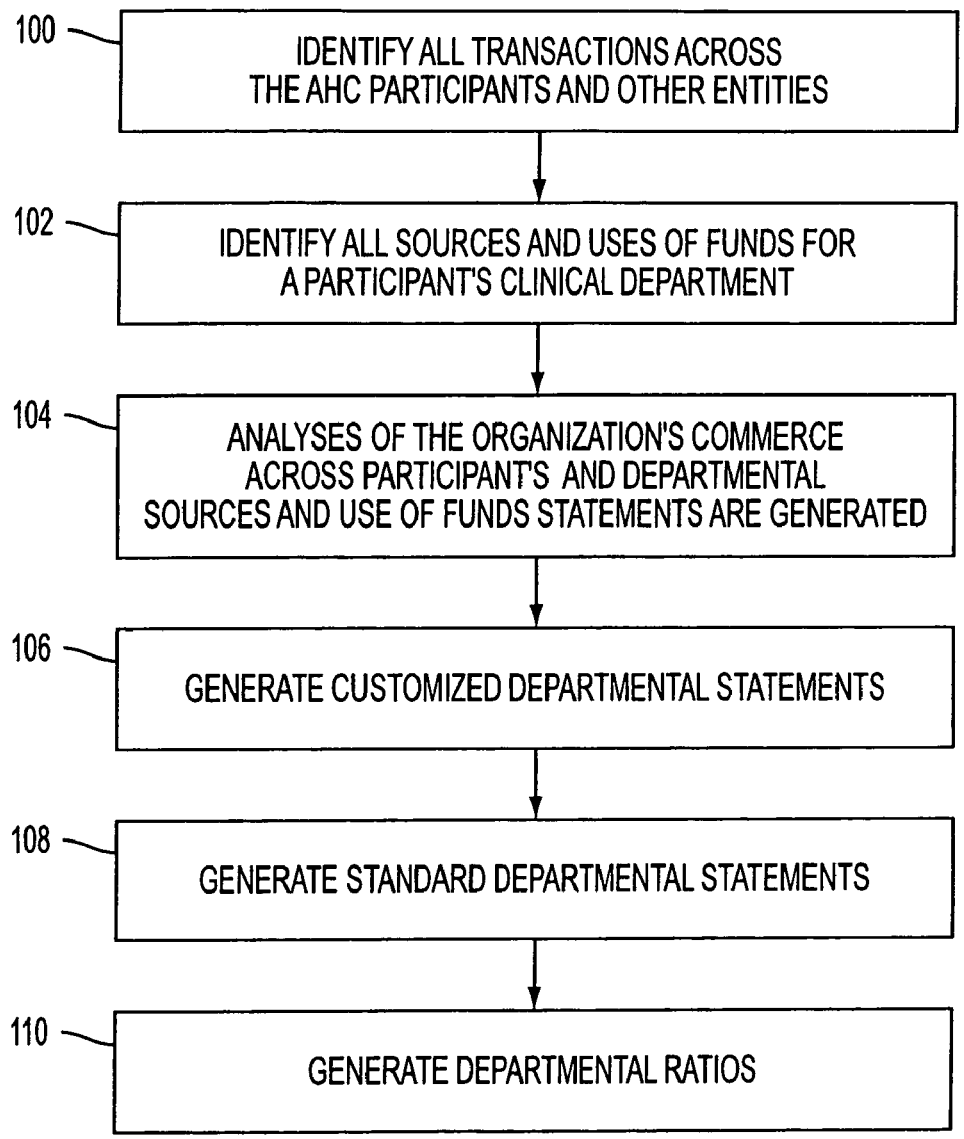
FIG. 2 is a flow chart of the steps of the present invention.

Referring to FIG. 2, a block diagram of the method for the present invention is illustrated. The method starts with identifying each transactions occurring across AHC participants (school of medicine 12, hospital 14, and faculty clinical practice 16 at step 100. This step also includes identifying transactions between the participants and parent university, government and other relevant entities. In addition, all sources and uses of funds for that participant's clinical departments are identified. Next, all sources and uses of funds for a participant's clinical department are identified at step 102. Then, an analysis of the organization's "commerce" across participants and departmental sources and uses of funds statements are generated at step 104. These are done in a manner that the participant deems relevant to understand and explain itself financially internally.

After all of the transactions have been correctly identified and categorized all its financial transactions, customized departmental statements are generated at step 106. Using defined logic and rules, relevant data contained in the customized departmental statements are used to generate standard departmental statements at step 108. The departmental statements are used to form the basis of the comparative database and are used to develop the comparative departmental ratios at step 110. Using the ratios and the other information, reports are generated for each participant.

In the most preferred embodiment, there are seven reports generated: custom triangle and supporting statements, standard triangle and supporting statements, customized departmental statements, standard department statements, departmental ratios by participants, ratios by department across participants, aggregate department sources and uses per FTE.

Referring back to step 102, all transactions between the participants which result in economic interdependencies need to be identified whether cash or non-cash. Cash transaction typically represent the following categories: support/funds provided; payment for service; and expense reimbursement or revenue passthrough. Non-cash transaction that represent a transfer of value include unreimbursed expenses and funds generated and retained. Unreimbursed expenses are expenses incurred on behalf of another operating activity that are requested or needed by that activity but are not charged back or reimbursed. Funds generated retained are funds generated from operating activities that are retained at executive or central levels.

By aggregating both cash and non-cash transactions as part of the analysis of the transfer of value ("funds flow") that occurs across missions of an AHC or between mission operating activities and the institution or community: spending on behalf of another entity has the same result in terms of a transfer of value as providing funds or receiving and retaining funds generated from another entity's operating activities as receiving funds.

Cash and non-cash "flow of funds" categories are further combined into two basic categories of support and payment for services. The support category consists of support given, unreimbursed expense and funds generated retained. The payment for services category consist of purchased services across operating activities, payment for central services and payment for clinical services. Purchased services across operating activities include physician leadership, physician service, physician incentives and non-physician services. The payment for central services are payments to the university, vice-president of health affairs (VPHA) and health system. The payment for clinical services includes payments from government, e.g., state, county and community.

Figure 3A:
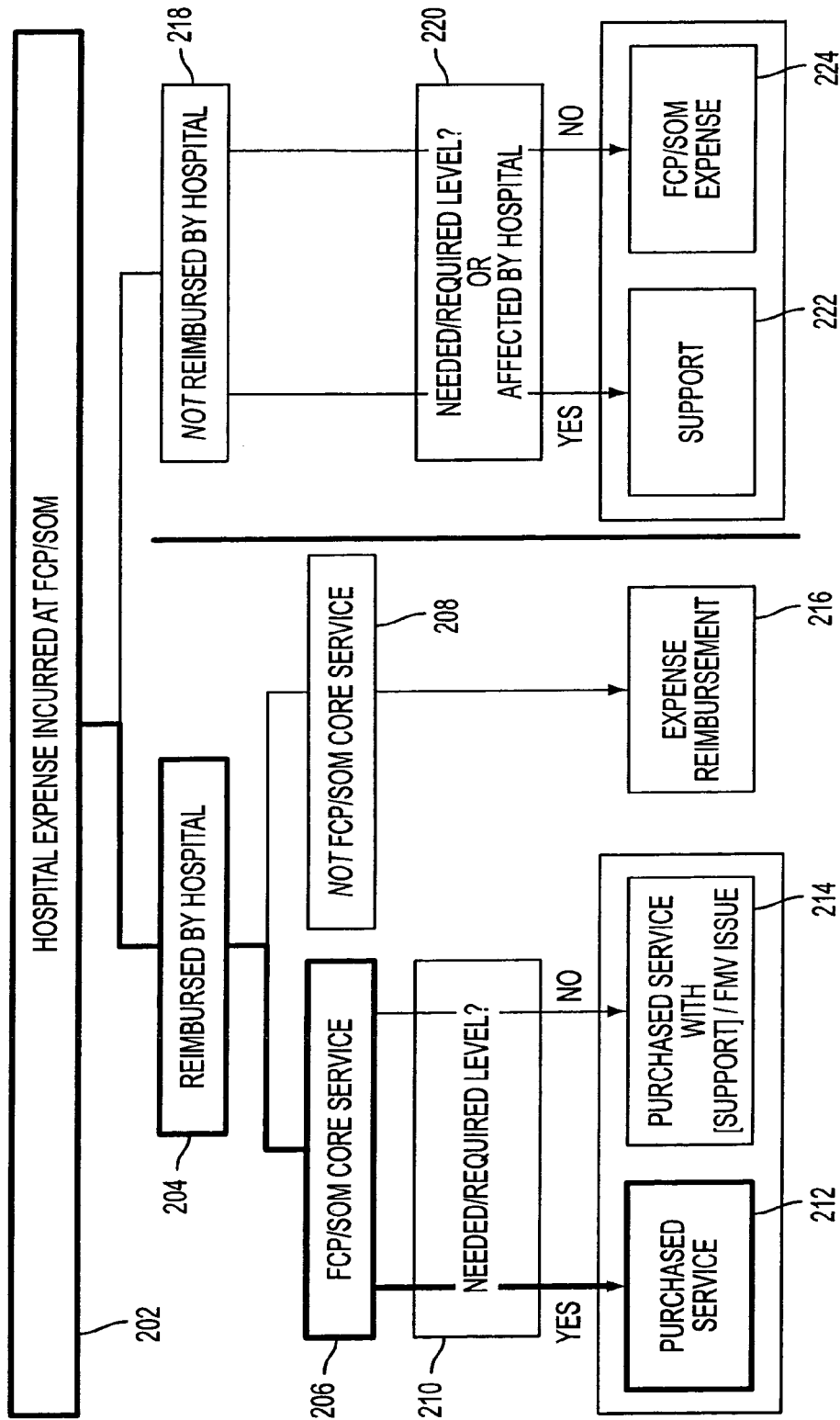
FIG. 3A is a block diagram for the payment for service definition.

Referring to FIG. 3A, a block diagram of the payment for service definition from the hospital's perspective is illustrated. For a hospital expense incurred at either the faculty care practice or school of medicine 202, the hospital must decide whether to reimburse the participant for the expense or not. For reimbursable expenses 204, the expense is for either a faculty clinical practice or school of medicine core service 206 or not for a faculty clinical practice or school of medicine core service 208. If the core service is needed or required 210, then the service is considered as a purchased service 212. If the core service is not a needed or required, then the service is a purchased service with the fair marker value needing to be determined 214. Thus, an entity would pay for another entity for core service at the appropriate level to support the buyer's mission operating activities (hospital clinical mission, faculty clinical mission, and school of medicine research and teaching missions).

Figure 3B:
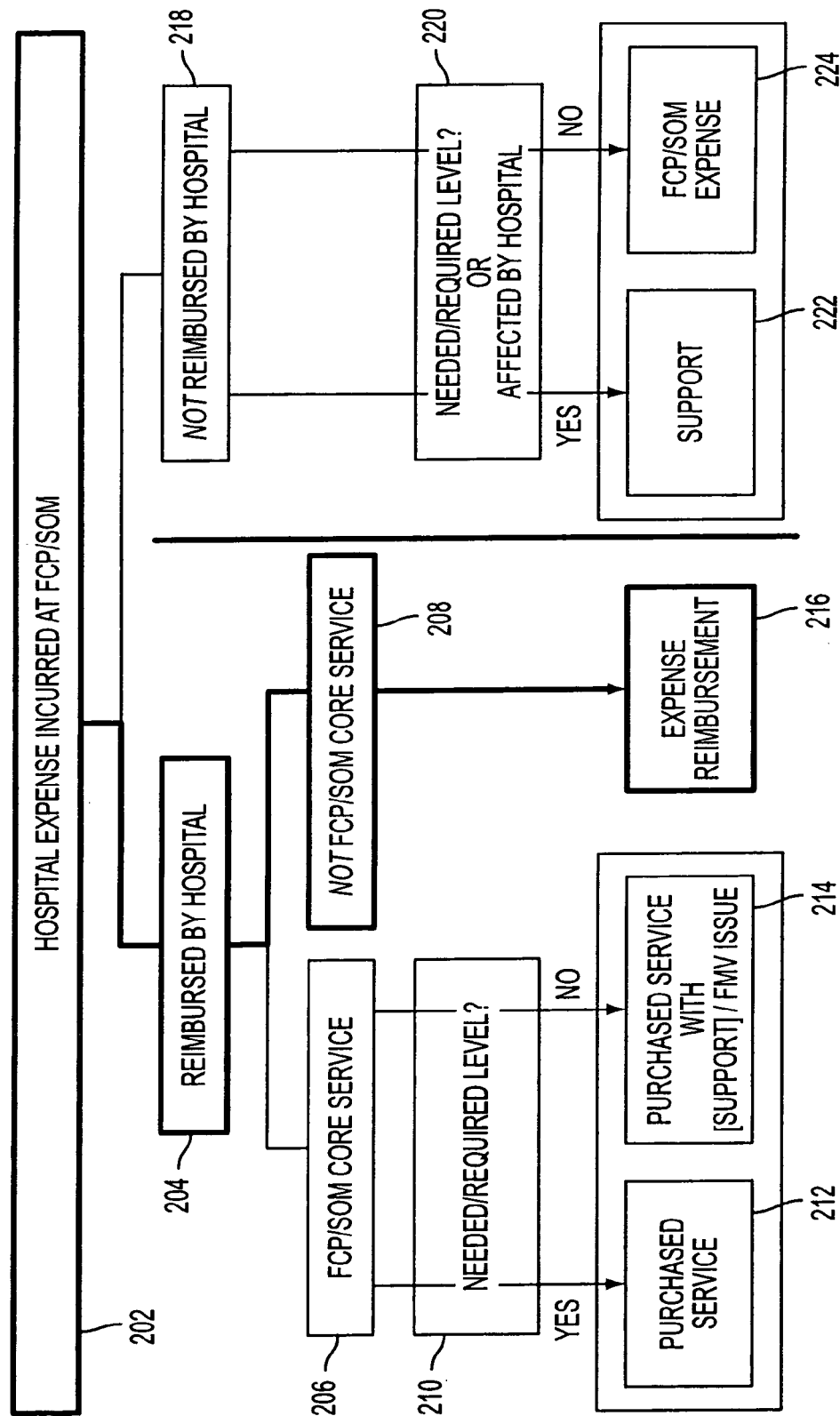
FIG. 3B is a block diagram for the expense reimbursement definition.

Referring to FIG. 3B, a block diagram of an expense reimbursement from the hospital's perspective is illustrated. For a hospital expense incurred at either the faculty care practice or school of medicine 202, the hospital must decide whether to reimburse the participant for the expense or not. For reimbursable expenses, the expense is for either a faculty clinical practice or school of medicine core service 206 or not for a faculty clinical practice or school of medicine core service 208. For a non-core service the expense is reimbursed 216. Thus, a participant would reimburse another entity's expenses that support the buyer's mission operating activities but are not core services for the seller.

Figure 3C:
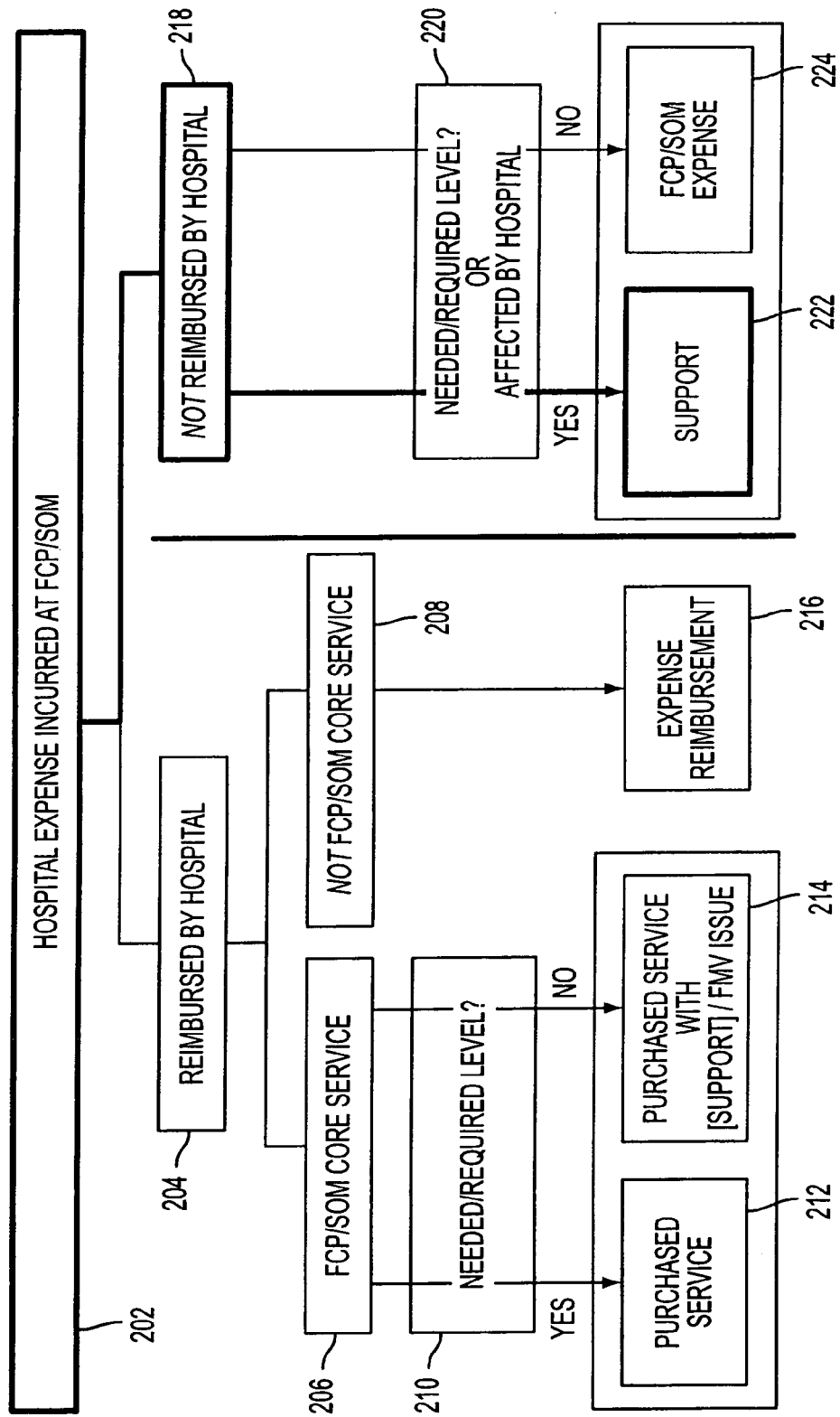
FIG. 3C is a block diagram for the support-unreimbursement definition.

Referring to FIG. 3C, a block diagram of an unreimbursed expense for support from the hospital's perspective is illustrated. For a hospital expense incurred at either the faculty care practice or school of medicine 202, the hospital must decide whether to reimburse the participant for the expense or not. For non reimbursable expenses by the hospital 218, the expense is labeled as support 222 if it is need or affected by the hospital 220 and expense is considered a faculty clinical practice or school of medicine expense 224 if it was not needed or affected by the hospital 220. Thus, expenses incurred on behalf of another operating activity (people, space, service, capital) that are requested or needed by that activity are reimbursed.

Figure 4:
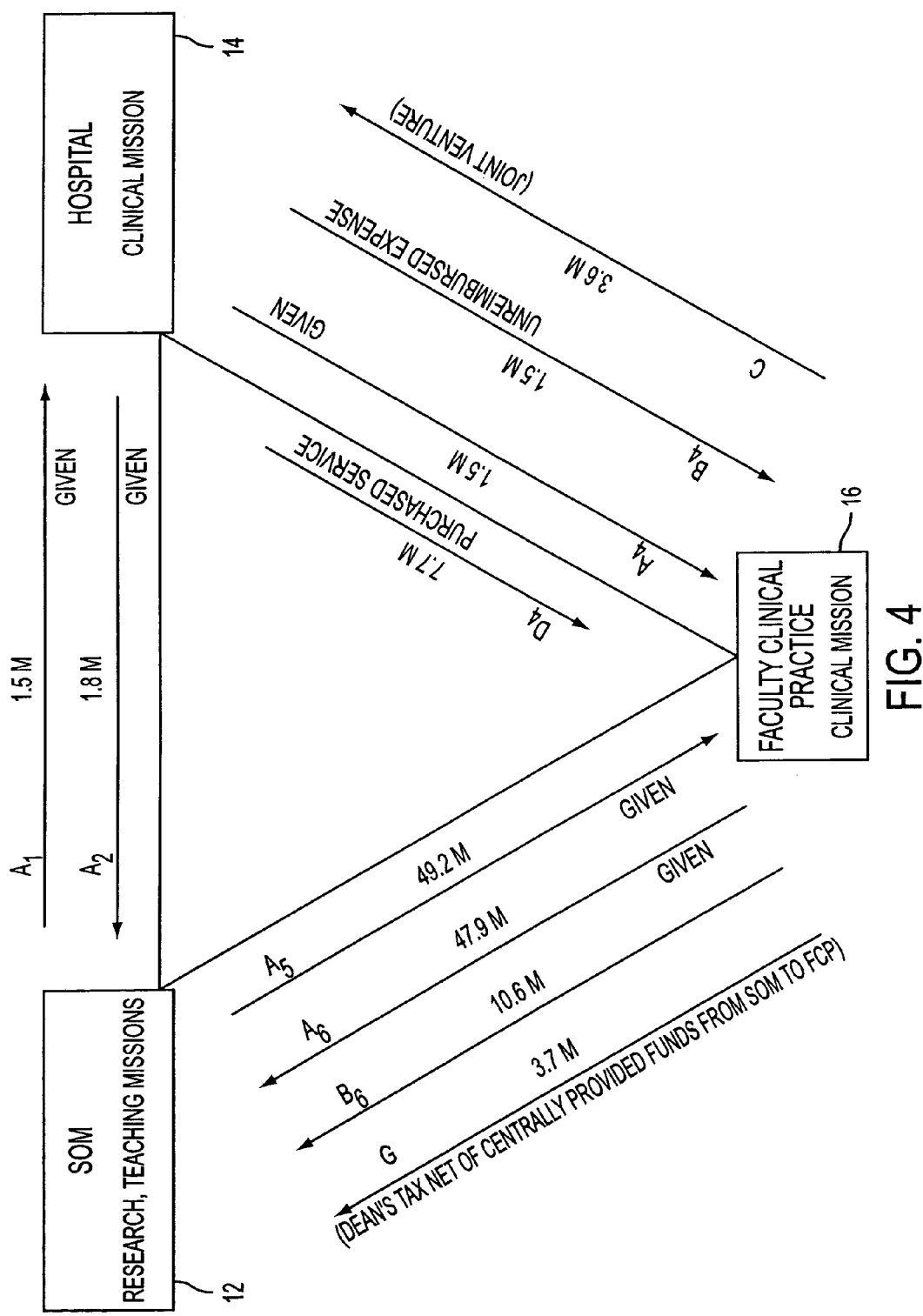
FIG. 4 is a block diagram of a financial model/logic for support and purchased services across operating activities.

As depicted in FIG. 4, a financial model/logic for support and purchased services across operating activities is illustrated. Each participant provides support categorized as support given A and unreimbursed expenses B to other participants. The support given A is broken into two categories: the funds the hospital 14 provides to the school of medicine 12 for investment in programs and services; and the funds faculty clinical practice 16 clinical department provides to the school of medicine 12 clinical department counterpart (transfers and contributions). The unreimbursed expenses B is broken into four categories: the expenses the school of medicine 12 provides for the teaching and supervision of residents to the hospital 14 without reimbursement; the expenses the hospital 14 spends employing the physician assistants and nurse practitioners who benefit the faculty clinical practice 16; the expenses the faculty clinical practice 16 provides medical direction to the hospital 14 without reimbursement; and the faculty clinical practice 16 incurs related to research and teaching (e.g., payment of faculty salaries, non-faculty salaries, supplies, etc).

In addition, joint venture support C is provided between the faculty clinical practice 16 and the hospital 14 based on differing levels of reimbursement for patient populations including indigent and Medicaid. There also funds generated retained G which are funds from the school of management to faculty clinical practice 16. The funds are the dean's tax net of centrally provided funds.

The purchased services D across the operating activities include services for physician leadership, physician services, physician incentives and non-physician services. The hospital 14 pays the school of medicine 12 for teaching and supervising residents. The hospital 14 pays the faculty clinical practice 16 for medical direction, professional service (e.g., emergency room, pathology, etc.) and gainshare and incentive programs with faculty clinical practice 16 departments and physicians 16.

Figure 5:
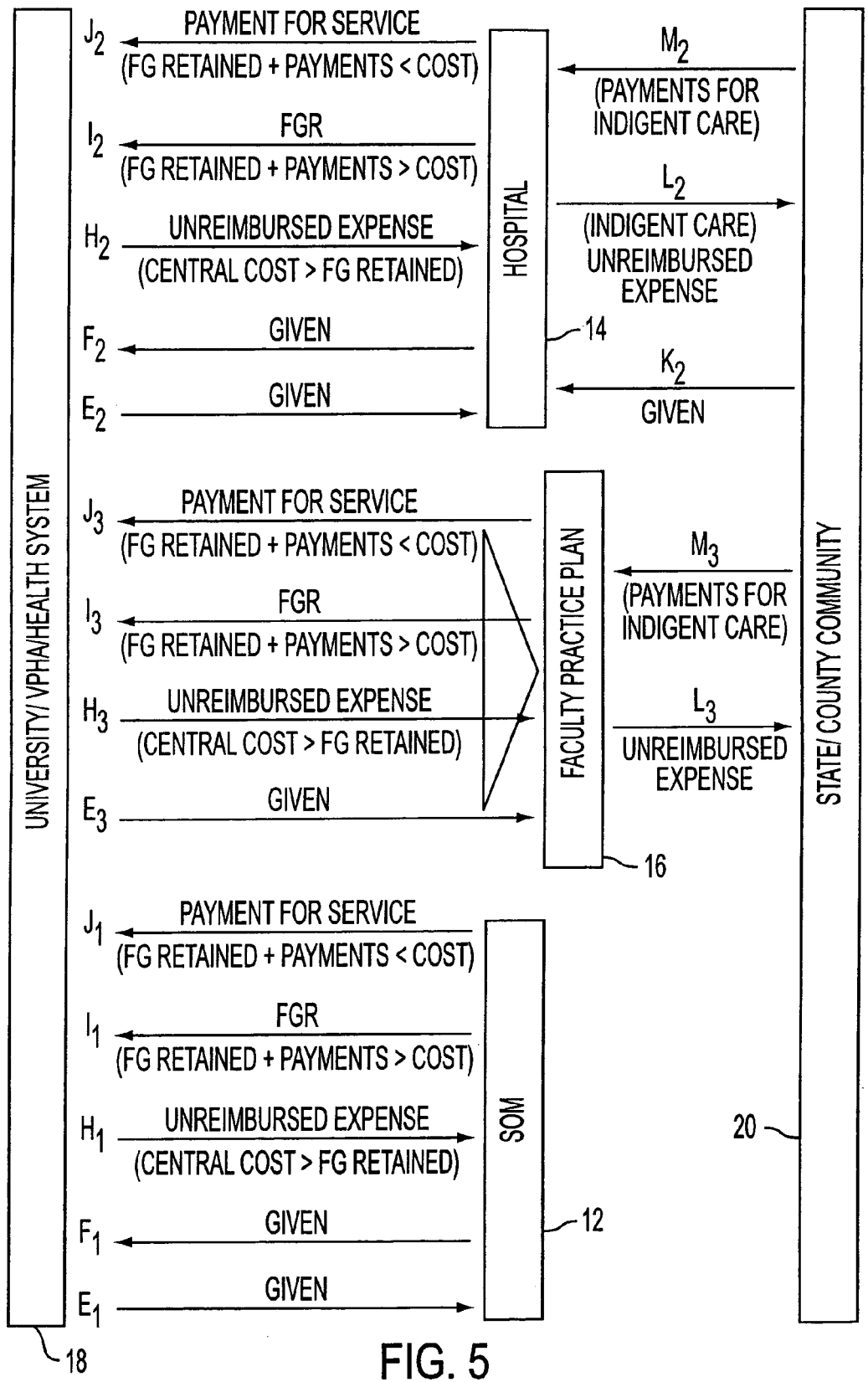
FIG. 5 is a block diagram of a financial model/logic for support and purchased services between operating activities and university, VPHA, health system or state, county and community.

Referring to FIG. 5, a financial model/logic for support and purchased services between operating activities and university, VPHA, health system 18 or state, county and community 20 is illustrated. Support includes support given E, F and K, unreimbursed expenses H and L and funds generated retained. Support given E, F, and K include: the state/university 18 providing annual funding to the school of medicine 12 for investment in programs and services; the hospital 14 providing funding to other university areas 18 (e.g., School of Nursing, School of Allied Health Provisions, etc.) for investment in programs and services; and the state 20 and university 18 providing funding to the hospital 14 for investment in programs and services. The unreimbursed expenses H includes the university providing central services at a level which exceed funds generated retained from the departments (e.g., tuition and fees retained, indirect cost recovery retained, etc.). The unreimbursed expenses L includes expenses incurred by the hospital 14 for provision of indigent care which exceeds reimbursement provided by the state and the expenses incurred by the faculty clinical practice 16 for provisions of indigent care which exceeds reimbursement provided by the state 20. The funds generated retained I include the funds the university retains from the funds generated by the department (e.g., tuition and fees retained, indirect coast recovery retained) at a rate which exceeds the value of services provided by the university 18.

The payment for services include funds generated retained J and indigent care payment for service N. The funds generated retained include funds the university retains from the funds generated by the department (e.g., tuition and fees retained, indirect cost recovery retained, etc.) at a rate less than or equal to the value or services provided by the university 18. The indigent care payment for service includes the funding/reimbursement the state provides the hospital 14 for the provision of care to patient populations including indigent and Medicaid and the funding/reimbursement to the faculty clinical practice 16 for the provision of care to patient populations including indigent and Medicaid.

Referring to FIG. 6, a table of the transactions is illustrated. The exemplary table provides information about the transactions including who is providing who funding (from/to), an index numbering each transaction, an ACT index number, whether the funds are given or are payment for service (S, PS), the description of the transaction, the amount of the transaction, and the source of the funding.

As depicted, indexes $A_4$, $B_4$ illustrate the support the hospital 14 gives to the faculty clinical practice 16. Index $A_4$ consists of $1.5 M given for an ASC list. Index $B_4$ consists of $1.5 M gives for hospital based clinics, enterprise-wide marketing, and enterprise-wide contracting. Index $D_4$ depicts the amount ($7.7 M) the hospital 14 pays the faculty clinical practice 16 for services. The services are gain sharing and the emergency room contract of the ASC list. Index C depicts the funds ($3.6 M) the faculty clinical practice 16 provides to the hospital 14.

Index $A_2$ depicts the support ($1.8 M) the hospital 14 gives the school of medicine 12. The support is given for the ASC list. In turn, index $A_1$ depicts the support ($1.5 M) the school of medicine 12 gives the hospital. This funding is for supporting the residency program.

Index $A_5$ depicts the support ($49.2 M) the school of medicine 12 gives the faculty clinical practice 16. The support is given for the faculty salaries paid out of the clinical funds and clinical expenses. In turn, index $A_6$ depicts the support ($47.9 M) the faculty clinical practice 16 gives the school of medicine 12. This funding is for supporting the net income transfer. Index $B_6$ depicts the support ($10.6 M) the faculty clinical practice 16 gives the school of medicine 12. The support is given for paying the faculty salaries for research and teaching from the clinical mission. Index G depicts the support ($3.7 M) the faculty clinical practice 16 gives the school of medicine 12. The support is given for paying the dean's tax.

Index $M_2$ depicts the support ($73.2 M) the state 20 pays the hospital 14 for services. The services are for the net revenue for indigent care and tobacco tax revenue. Index $L_2$ depicts the support ($21.9 M) the hospital 14 gives the state for unreimbursed indigent care and additional losses the hospital 14 incurs due to resetting indigent care. Index $K_2$ depicts the support ($18.5 M) the state 20 pays the hospital 14 for services. The services are for the Medi-CAL graduate medical education (GME) funds and clinical teaching support. Index $J_2$ depicts the support ($2.9 M) the hospital 14 pays the university 18 for services. The services are for the central services charged.

Index $M_3$ depicts the support ($7.9 M) the state 20 gives the faculty clinical practice 16 for cost in excess of reimbursement for payments received for indigent care. Index $L_3$ depicts the support ($3.6 M) the faculty clinical practice 16 gives the state for cost in excess of reimbursement for indigent care and reimbursement gained in resetting indigent care. Index $J_3$ depicts the support ($0.6 M) the faculty clinical practice 16 pays the university 18 for services. The services are for the central services charged.

Index $I_1$ depicts the support ($8.6 M) the school of medicine 12 pays the university for services. The services are for the ICR retained, tuition and fees received and expenses at the university. Index $E_1$ depicts the support ($49 M) the university 18 gives the school of medicine 12 for state funds and expenses at the dean.

Referring to FIG. 7, a chart of the internal commerce between the operating activities for each type of service is illustrated. This chart is created by using the information from the previous charts and tables. The rows consists of the purchased services, e.g., physician leadership, physician service, physician incentive, non-physician, and supervision and teaching. The columns consist of who provided the services and who received the services, e.g., hospital to school of medicine, hospital to faculty clinical practice, school of medicine to faculty clinical practice, school of medicine to hospital, faculty clinical practice to hospital and faculty clinical practice to school of medicine.

Referring to FIG. 8, a summary sheet is illustrated. The sheet organizes the information from the chart illustrated in FIG. 6. As shown, the transactions between the different operating activities are shown. Similarly, the transactions between the operating activities and the university/VPHA/Health System and the transactions between operating activities and the government (state/county/community) are illustrated. These transactions are categorized as either support or payment for support. The support category is further broken into four categories/columns: given, unreimbursed, funds generated retained > centrally provided, and joint venture. A sum of these four categories is in a total column.

At the bottom, the total of each category is tallied for each column is calculated for each operating center, as well as for the university/VPHA/Health system and government. If the totaled figure is a gain, then the figure is labeled as net support and for losses, the figure is labeled as net services purchased from (sold).

Figure 9:
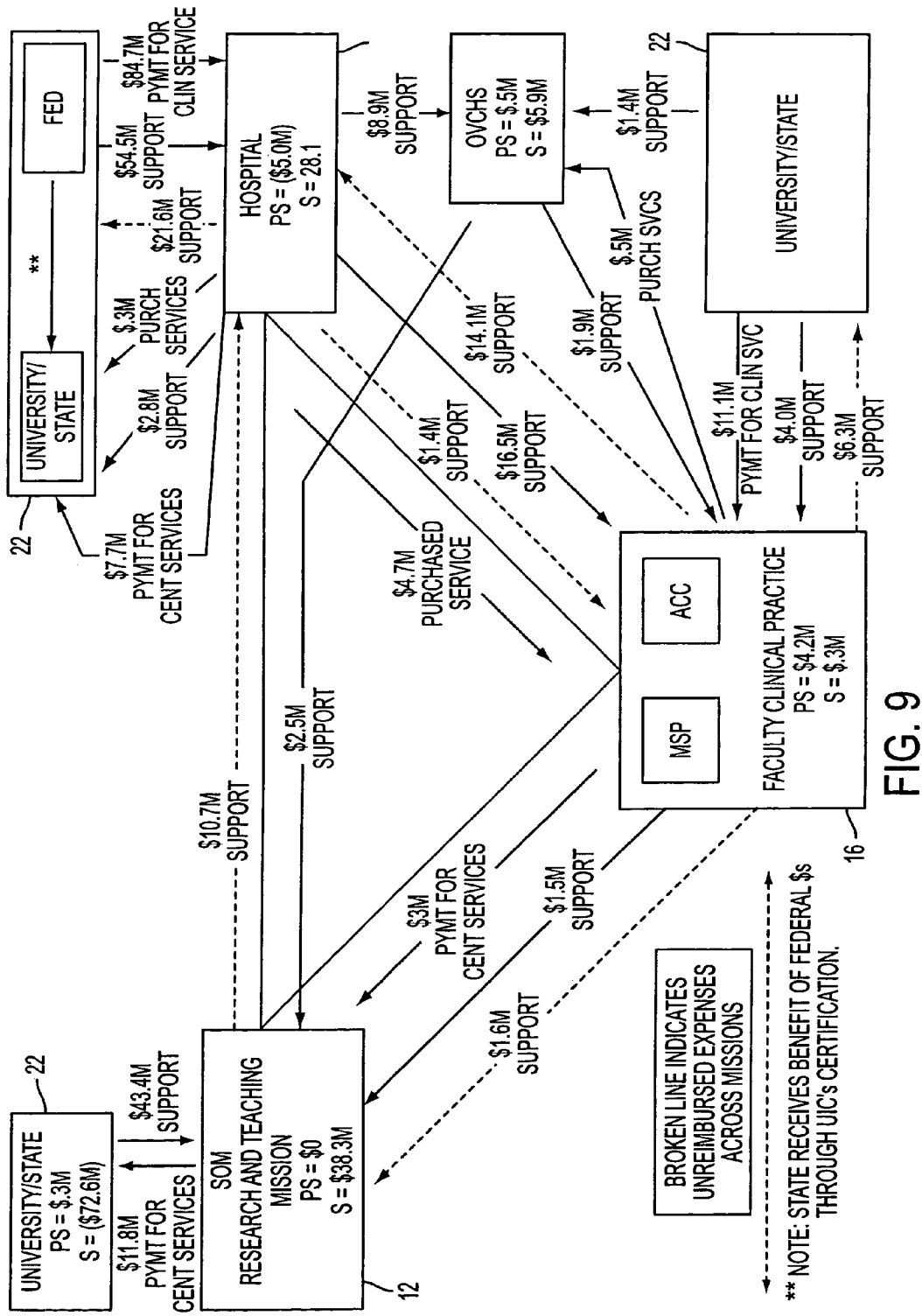
FIG. 9 is a block diagram of a financial model/logic for support and purchased services across and between operating activities.

Referring to FIG. 9, a financial model/logic for support and purchased services across and between operating activities is illustrated. The cash and non-cash transactions are aggregated into three basic levels: across mission operating activities (school of medicine 12, hospital 14, and faculty clinical practice 16); between mission operating activities and the university/state 22 and between the operating activities and the office of the vice-chancellor health systems (OVCHS) 24.

Referring to FIGS. 10A–E, charts of the fund flows for programs and services across operating activities is illustrated. The exemplary table provides information about the transactions including an index numbering each transaction, who is providing who funding (from/to), whether the funds are given or are payment for service (S, PS), the type of funding, the category of the funding, the amount of the transaction, the description of the transaction, the amount of the transaction, and the source and point of contact for the funding.

Referring to FIG. 10A, a chart having the funding flows for programs and services is illustrated. The hospital 14 gives funding support to the faculty clinical practice 16 for state appropriations and state paid benefits to model clinics at the hospital's discretion; state appropriations passed through (cash) and benefits (non-cash); joint venture clinic operations; and contracts between the hospital 14 and school of medicine clinical departments and faculty including salaries (cash) and benefits (non-cash) for medical directorships, chiefs of service, program directors, as well as for investment in program and services. Funds for the joint venture clinic operations include funding for sharing losses and profits, annual reconciliation verse quarterly (cash flow), expected verse actual collections and medical doctors professional fees (based on sharing formula); low indirect cost/overhead rate, and payment for ambulance care medical directorships. There is also unreimbursed expenses between the hospital 14 and the faculty clinical practice 16 for program and services. These expenses include billing which is 8% of net revenue (non-cash) and A/R funding which is 5% for 80 days (non-cash). The faculty clinical practice 16 has unreimbursed expenses with the hospital 14 for faculty effort benefiting the hospital 14 and unfunded medical direction salaries and benefits (non-cash). There is also an unquantified amount which is inherent in the AMC system, for lack of standardization and equipment.

Referring to FIG. 10B, a chart having the funding flows for the office of the vice chancellor of health system (OVCHS) and strategic investment fund (SIF) is illustrated. The hospital 14 provides funding support to the OVCHS for funding of the strategic investment fund (SIF) net of expenditures on hospital projects. The hospital 14 also incurs unreimbursable expenses on behalf of the faculty clinical practice 16 for funding the OVCHS office. The OVCHS, in turn gives support to the faculty practice clinic 16 for SIF expenditures, faculty salaries (cash), faculty benefits (non-cash) and other expenditures (cash). The OVCHS also gives support to the school of medicine 12 for SIF expenditures, faculty salaries (cash), faculty benefits (non-cash) and other expenditures (cash). The faculty clinic practice 16 pays the OVCHS for services. These services are for funding from MDs for marketing (cash).

Referring to FIG. 10C., a chart having the funding flows for public aid and for the prisoner population is illustrated. The state funds the hospital 14 and faculty clinical practice 16 for clinical services for the public and prisoners. However, both the hospital 14 and faculty clinical practice 16 incur unreimbursed expenses in supporting these clinical services. The unreimbursed expenses are a result in the shortfall of the public aid and prison population before reimbursement reset. There is also expenses incurred from the reimbursement foregone under reset.

Referring to FIG. 10D, a chart having the funding flows for research and training is illustrated. The hospital 14 incurs an unreimbursed expense for supporting the school of medicine 12. This expense is for clerical and other support for the research. The school of medicine 12 also pays the hospital 14 for hospital services for research for such items as beds, labs, x-rays, etc. The faculty clinical practice 16 gives funding support to the school of medicine 12. The funds are for the dean's tax (cash) of the net of services provided. In addition, the faculty clinical practice 16 incurs an unreimbursed expense for payment of faculty salaries and benefits for research efforts, as well as payment of non-faculty salaries and benefits for research and teaching efforts. The faculty clinical practice 16 incurs unreimbursed expenses for faculty effort benefiting the hospital 14, e.g. committee meetings. Similarly, school of medicine 12 also gives support to the hospital 14 for its residency program. As a result, the school of medicine 12 incurs unreimbursed expenses for faculty effort benefiting the hospital 14, e.g. supervision of house staff.

Referring to FIG. 10E, a chart having the funding flows for central provided services is illustrated. The university/state support the school of medicine 12 (including the basic science departments) with state appropriations to the departments for research and teaching (cash) and state paid benefits (non-cash). The university/state support the hospital 14 with state appropriations (cash). The hospital 14 supports the university for other colleges, i.e., health professions, pharmacy, nursing (cash). The hospital pays the university/state for purchased service from the nursing and dentistry colleges (cash). The university/state support the hospital 14 for maintenance, utilities, and A&G (non-cash). The university/state support the OVCHS with state funding including excellence in academics (cash). The hospital 14 pays the university/state for services. These services are central service charges (i.e., overhead for university/campus administration). The school of medicine 12 pays for central services. The university/state supports the school of medicine 12 for services provided in excess of funds generated retained (non-cash). The faculty clinical plan 16 pays the school of medicine 12 for services including dean's tax applied toward services provided by the dean for the faculty clinical practice 16 (cash).

Referring to FIG. 11, a table of the purchased services and support by the hospital is illustrated. Using the above information from the tables/charts, an exemplary table listing the purchased services by the hospital (cash), the purchased service by the hospital (benefits—non-cash), medical service plan (MSP) support to the hospital (non-cash), MSP support to the hospital (benefits—non-cash), total salary value of the services provided to the hospital, total benefits value of the service provided to the hospital, hospital support to MSP (cash), hospital support to MSP (benefits—non-cash); hospital cash payments to MSP, hospital non-cash payments to MSP, and total hospital cash and non-cash payments to MSP are listed in columns for each department, listed in the rows. Each column is tallied, and the total cash payments per salary schedule (excluding ambulance care medical directorships) are determined as well as the variance.

Referring to FIGS. 12A–B, a chart of the strategic investment fund is illustrated. This columns are broken into the expenditures/transfers out, department attributed for funds flow, UIC attribution by department, description, school of medicine, hospital, MSP, faculty salaries for the school of medicine, all other school of medicine, faculty salaries for MSP, all other MSP, and the total. The rows are broken into different administrations and the hospital's administrations. Each column is tallied to determine the total expenditure/transfer out of the different entities.

Referring to FIG. 13, an exemplary list of the reporting departments is illustrated. For reporting, data is collected at any level which will be useful for internal analyses. In the preferred embodiment, every effort is made to report separately all departments and sections indicated with an * and some departments may be rolled into a parent party. In the preferred embodiment, data is collected for the following departments: anesthesiology*, dermatology*, emergency medicine*, family medicine*, internal medicine*, neurology*, obstetrics/gunecology*, pediatrics*, physical medicine/rehabiliaton medicine*, psychiatry*, radiology*. Pathology*, and surgery*. Internal medicine is a parent department and includes general internal medicine, cardiology*, endocrinogy/metabolism, geriatrics, gastroenterology*, hematology/oncology*, infectious diseases, nepharology, pulmonary disease*, and rheumatology. Obsterics/gynecology is a parent department and includes gynecology oncology, maternal and fetal medicine and reproductive endocrinology. Pediatrics is a parent department and includes general pediatrics, pediatric cardiology, pediatric critical care, pediatric endocrinology, pediatric gastroentrology, pediatric neonatal medicine, pediatric neorology, and pediatric pulmonology. Radiology is a parent department and includes nuclear medicine, radiation oncology* and diagnostic radiology*. Pathology is a parent department and includes anatomic pathology, clinical pathology and basic science. Surgery is a parent department and includes cardiovascular surgery, general surgery, necrological surgery*, ophthalmology*, orthopedic surgery*, otorhinolaryngology*, pediatric surgery, plastic surgery, urology*, and vascular/thoracic surgery.

Figure 14:
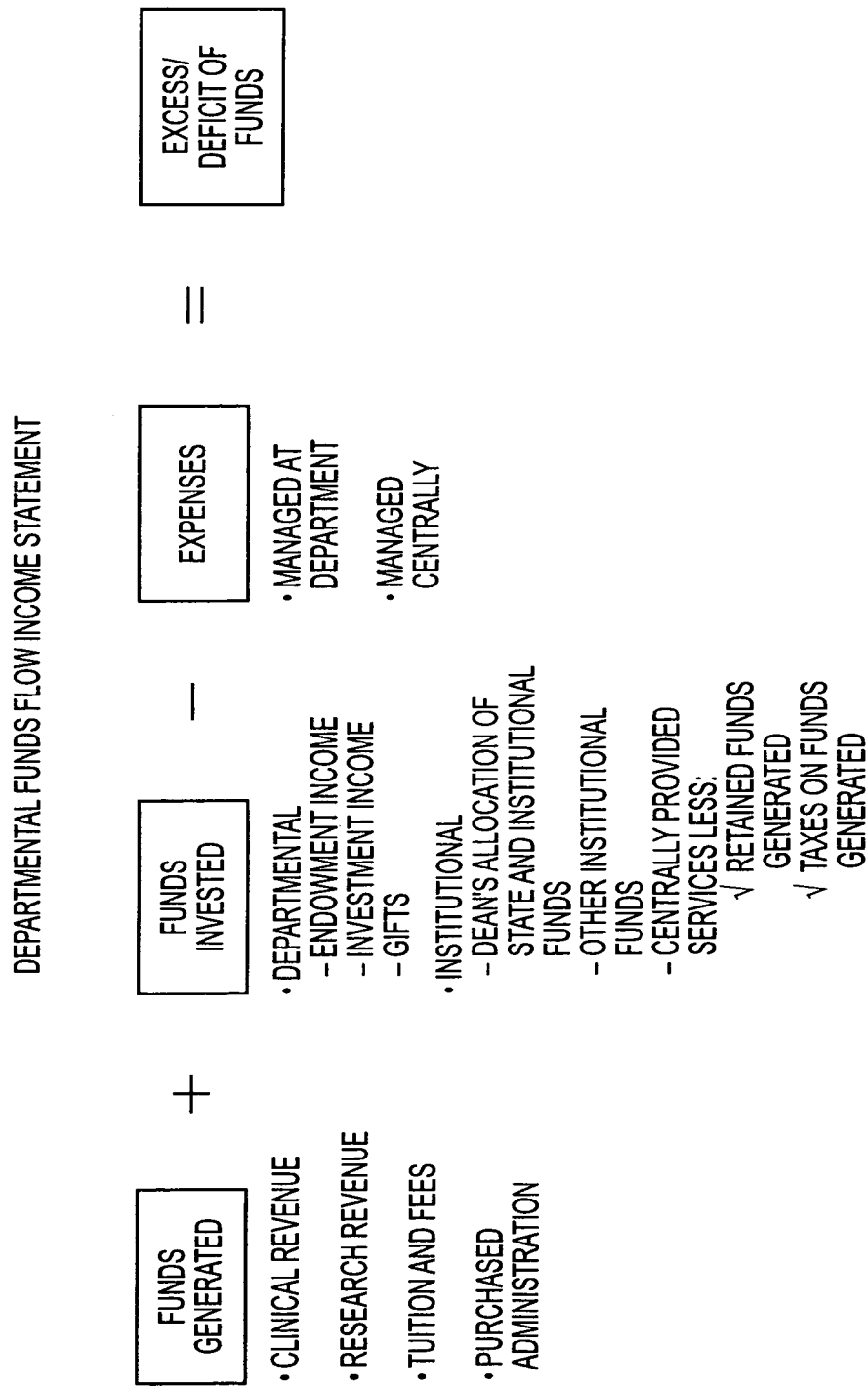
FIG. 14 is a block diagram of a departmental funds flow income statement.

Referring to FIG. 14, an exemplary departmental fund flow income statement is illustrated. As depicted, the excess or deficit funds is the funds generated by the department plus the funds invested in the department minus the department's expenses. In this example, the funds generated include clinical revenue, research revenue, tuition and fees, and purchased administration. The funds invested include departmental and institutional funds. Departmental funds include endowment income, investment income and gifts. Institutional funds include the dean's allocation of state and institutional funds, other institutional funds, centrally provided services less retained funds generated and taxes on funds generated. Expenses include expenses managed at the department as well as expenses managed centrally.

Referring to FIGS. 15A–B, sources of funds for the school of medicine 12, both externally funded research and other academic areas and the faculty clinical practice 16 are illustrated. Externally generated funds are defined as funds generated from external sources related to current operating activities of the research, teaching and clinical missions. External funds include net patient care revenue, direct expense reimbursement—Federal and non-Federal, indirect cost recovery—Federal and non-Federal, tuition and fees, direct paid salaries, other externally generated funds.

Line 1 is the Net Patient Care Revenue which includes revenue generated from patient care activities. Lines 2 and 3 are Direct Reimbursement (DER), Federal and non-Federal, which include the portion of grant and contract funding for direct expenses (expenses received directly at the department and accounted for at the department). Grant and contract funds are attributed to research, teaching (e.g., teaching and training grants) or clinical (e.g., public service contracts to provide clinical care) mission activities. Direct expense reimbursement is identified separately for Federal and non-Federal funding sources. Lines 4 and 5 are Indirect Cost Recovery (ICR), Federal and non-Federal, which are portions of grant funding for institutional overhead expenses. Indirect cost recovery is identified separately for Federal and non-Federal funding sources. Line 6 is Tuition and Fees which are student payments for tuition and fees allocated to a department. Payments are not received directly at the departments are reported here and will have an equal amount on Line 29 in the "Funds Generated Retained" section. Line 7 is the Direct Paid Salaries which are faculty compensation received directly form external sources related to current operating activities of the research, teaching or clinical missions (e.g., Veteran Administration direct paid salaries for patient care services). There will be an equal expense amount reported as line 44—Direct Paid faculty Salaries and Benefits). The other externally generated funds in lines 8a and 8b are other external funds related to research, teaching and clinical mission activities not included in lines 1–7. Line 10 is the subtotal which is calculated by adding lines 1–8.

Internally generated funds are defined as funds generated from the internal sale and purchase of services related to research, teaching and clinical missions. For example, a hospital 14 may purchase medical director services or other physician leadership activities. Internal funds generated includes payments received for services (lines 11 and 12) as well as unreimbursed services (lines 13 and 14). Sale and purchases of services involving the hospital 14 are include in line 11. Unreimbursed services involving the hospital 14 are included in line 13. Unreimbursed services will have an equal offsetting amount recorded on lines 34 or 35 as support to other operating units. Line 16 is the subtotal which is calculated by adding lines 11–14. Line 17 is the total funds generated which is calculated by adding lines 10 and 17.

Institutional Investment includes funds committed to a program or department from University, Health System, Dean or other executive/central level sources. These include funds provided and expenses incurred on behalf of departments that are in excess of external funds generated related to department research, teaching and clinical mission activities that are retained or taxed by executive/central levels.

Lines 18–21 are funds provided from the University, Health System, Dean and other sources. These funds are provided by the executive level sources to a program or department, e.g., Dean's allocations and commitments. Line 22 is the subtotal which is calculated by adding lines 18–21.

Lines 23–26 are expenses incurred on behalf of a department from the University, Health System, Dean and other sources. Overhead and centrally managed expenses incurred on behalf of departments at executive and administrative/central levels that are not charged to departments, e.g., centrally provided services, dean's office expenses, etc. Line 27 is the subtotal which is calculated by adding lines 23–26.

Lines 28–30 are funds generated retained from the research/ICR retained, teaching and clinical. External funds generated related to department research, teaching and clinical mission activities that are retained or taxed by executive levels, e.g., ICR or tuition and fee revenue retained at executive/central levels, dean's taxes on clinical revenues, taxes on internal transactions, interest income on clinical funds retained at executive levels. Line 31 is the subtotal which is calculated by adding lines 28–30.

Lines 38–35 are directed to support between AMC operating units and include: funds committed to a program or department from other operating units (hospital 14s, school of medicine 12, faculty clinical practice 16); expenses incurred at the operating level on behalf of another operating unit that are not reimbursed; and unreimbursed services across operating units reported on lines 13 or 14. Transaction involving the hospital 14 are separately identified. Line 32 are funds committed to a program or department from other operating units, involving the hospital 14. Line 33 are funds committed to a program or department from other operating units, not involving the hospital 14. Line 34 are expenses incurred at the operating level on behalf of another operating unit that are not reimbursed, involving the hospital 14. Unreimbursed services across operating units reported on line 13. Line 35 are expenses incurred at the operating level on behalf of another operating unit that are not reimbursed, not involving the hospital 14. Unreimbursed services across operating units reported on line 14. Line 37 is the subtotal which is calculated by adding lines 32–35.

Lines 38–40 are directed to departmental investment which includes: funds committed to operative activities from departmental non-operating; funds committed to operative activities from departmental operating sources across missions; and expenses incurred within a department on behalf of another mission that are not reimbursed. Line 38 are funds committed to operative activities from departmental operating sources across missions, e.g., transfers from faculty clinical practice 16 to support research and teaching missions within a department. Line 39 are expenses incurred within a department on behalf of another mission that are not reimbursed, e.g., payment of faculty salaries from clinical mission funds in excess of effort at the clinical mission. Line 40 are funds committed to operating activities from departmental non-operating sources, e.g., use of endowment or interest income earnings, use of prior period reserves, patent and royalty income. Line 41 is the subtotal which is calculated by adding lines 38–40. Line 42 is the total funds invested. Line 43 is the total for the sources of funds.

Referring to FIG. 15C, uses of funds for the school of medicine 12, both externally funded research and other academic areas and the faculty clinical practice 16 are illustrated. Lines 44–56 are directed to funds managed at a department which includes expenses managed at the department. Line 44 reflects direct paid salaries from sources outside the AMD, e.g., Veteran Administration direct paid salaries for patient care activities. Line 45 is an adjustment to an accounting firm to match effort by mission to faculty salary and benefit expense by mission. This is based on participant reported time and effort by mission and relationship of medical group management association (MGMA) faculty compensation expense to clinical mission production. Lines 46 and 47 reflect department paid faculty salaries and benefits, respectively. Lines 48 and 49 reflect department paid non-faculty salaries and benefits, respectively. Line 50 is the subtotal which is calculated by adding lines 44–49.

Line 51 are the expenses managed at the department not included in lines 44–49, e.g., non-compensation expenses. Line 52 is the indirect cost recovery money returned to the departments. Line 53 reflects the unreimbursed expenses supporting operating activities included in lines 34 and 35. Line 55 is the subtotal which is calculated by adding lines 51–53. Line 56 is the total managed at the department.

Lines 57–61 are directed to other sources of funds which include expenses managed at executive/central levels. Lines 57–60 reflect allocations of overhead and centrally managed services included in lines 23–26 and are directed to the university, health system, dean, and others, respectively. Line 61 is the subtotal which is calculated by adding lines 57–60. Line 62 is the total uses of funds. Line 63 is the total sources over or under the uses of funds. Line 64 is the use of the prior period reserves. Line 64 is directed to the use of prior period excess to support current operating period. This includes net transfers into current operating funds. Line 65 is the total sources over or under the uses of funds.

Using the above information, customized and standard statements can be generated. The key focus of the analysis is identification and quantification of the internal commerce occurring between the school of medicine, faculty practice, and hospital, as well as other entities, such as the parent university and government. Commerce includes monetary payments and services, which may or may not be charged.

A further refinement of the description of AHC commerce is to define all monetary and non-monetary transfers between corners of the triangle that represent investment/support, which is defined as a non reciprocal transfer which results in one operating unit receiving a benefit without experiencing a corresponding sacrifice, or a purchased service, defined as a reciprocal transfer or exchange in which an operating unit both receives a benefit and performs a service. A purchased service may have imbedded within it support. For example, one of the major types of purchased services identified is the payment to physician faculty for management and supervision of hospital units, e.g., the medical director function. In order to properly account for all the services, the fair market value (FMV) needs to be determined for the services.

The clinical department reports, whether customized or standard, follow the same logic: Customized Statements may contain sources or uses of funds, which the participant wishes to specifically identify—e.g., clinical income from a specific contract or support from an unusual source. In the Standard Departmental Statements, two mappings have taken place. First, the department or divisions have been aggregated into a specific set of clinical departments (See FIG. 13) Second, the line items under the Standard Departmental Statements are identical for each participant and all departmental sources and uses of funds have been mapped to appropriate common line items.

Referring to FIG. 16, an exemplary customized departmental statement for the anesthesiology department is illustrated. As shown, the left column are described with respect to FIGS. 15A–C. The rest of the columns are broken into the school of medicine, practice plan, hospital/ambulance accounts and the total. The school of medicine column is further broken down into research, other academic and GME columns. Each participant receives its own customized supporting statements. Additional examples of customized department statements for other departments are attached in appendix A.

Referring to FIG. 17, an exemplary standard departmental statement for the anesthesiology department is illustrated. As shown, the left column are described with respect to FIGS. 15A–C. The rest of the columns are broken into the school of medicine, practice plan, hospital/ambulance accounts and the total. The school of medicine column is further broken down into externally funded research and other academic columns. Each participant receives all the participants Supporting Statements. Additional examples of standard department statements for other departments are attached in appendix A.

From the standard departmental statements a series of ratios have been identified which construct a picture of a department's clinical and research productivity, its efficiency and its dependency on various forms of activity and support. Examples of productivity ratios include funds generated, research and clinical, per full time faculty member in the department; funds generated as a percentage of total sources of funds; research funds generated per funds invested.

Departmental ratios by participants are generated into a report. This report is constructed for each participant, showing its departments side-by-side for a given ratio analysis. In addition, ratios by department across participants are generated into a report. This report is constructed by department, showing the participants side-by-side for a given ratio analysis. Each participant receives the ratios for all participants for comparison. An aggregate of department sources and uses per FTE is generated into a report. This report is an aggregate of different clinical departments—it is not for any particular participant. It provides sources and uses information on an FTE basis that can be used to construct analyses of a participant's department relative to the aggregate benchmark data from all participants.

The reports can be provided in a variety of manners. In one embodiment, the reports are provided as hard copies. In yet another embodiment, the reports are provided on a memory medium such as a floppy disk or compact disc. In the preferred embodiment, the reports are available via a network, such as the Internet. Providing the reports via an electronic media, such as either of the later embodiments, the individual participants to re-arrange and re-analyze the date to meet local educational and management needs. Several participants have already determined which key measures they wish to track and provide to enterprise leadership. To support this activity, each participant also receives a series of diskettes containing the seven funds flow reports in a digital format.

Participants use the deliverables from the funds flow project in a number of ways. The analyses help quantify the value of the clinical mission. A number of previous participants have used these results to explain the AHC clinical enterprise to external constituencies. The data can be used to support negations and to rationalize contracting between the system participants. The results are especially intended to support analyses of departmental operating issues and promote departmental accountability.

Implementation of information from the funds flow analysis is the most challenging aspect of the project. Experience of early participants is that all funds financial management promoted by this activity evolves over several years. First, a knowledge base of clinical enterprise flow of funds and departmental financing needs to be established, with validation and acceptance by interested parties. The financial management concepts and tools provided by the analysis need to be incorporated into the organization's way of doing business. At this point, the organization is ready to revisit and revise investment and support arrangements that have been identified and begin to establish goals and manage under new accountabilities. The latter usually occurs when the organization undertakes mission-based budgeting and the other participants of mission-based financial management.

A standardized report can be generated for each participant. A standard report allows participants to be compared to other participants. Thus, an emergency room participant can compare itself with a pediatrics participant. On a larger scale, the emergency room participant can compare itself with another emergency room participant from a different AHC hospital 14. Such comparisons allow for benchmarking and allows for participants to determine how other participants handle similar costs and services, thus allowing participants to reduce costs and increase their service to costs ratios.

The categories of funding sources and uses as defined provide participants with the ability to analyze the total economics of mission operating activities and to compare productivity, efficiency and total investment in operating activities across participants. These analyses over time by participant and across participants are supported by the ability to identify total productivity, total investment, total expenses, institutional support and investment across missions.

The total productivity are the total funds generated from operating activities, whether received and managed at the department level or retained at administrative/executive/central levels to fund overhead and centrally managed activities that support mission operating activities. The total investment is the investment required to support operating activities, both funds provided to and expenses incurred on behalf of departments. Total expenses are the expenses supporting mission operating activities, including those managed at the executive or central levels and those incurred on behalf of departments. Institutional support is for the support in mission operating activities as funds provided plus expenses incurred directly on behalf of departments net of funds generated from operating activities that are retained at institutional levels to fund overhead and centrally managed services. The investment across missions occurs both across AMC operating units and within departments as well as investment in mission operating activities at the institutional level.

The following are the definitions for the key ratios, to determine productivity and efficiency, the following ratios are used: (1) External funds generated per faculty full time equivalent (FTE) is the ratio of the total external funds generated verse the full time equivalent faculty; (2) Internal funds generated per faculty full time equivalent (FTE) (excludes teaching and supervision of residents) is the ratio of the internal funds generated verse the full time equivalent faculty; (3) Total funds generated per faculty full time equivalent (FTE) (excludes teaching and supervision of residents) is the ratio of the total funds generated verse the full time equivalent faculty; (4) Clinical external funds generated per faculty full time equivalent (FTE) is the ratio of the total clinical external funds generated verse the full time equivalent faculty; (5) Research external funds generated per faculty full time equivalent (FTE) is the ratio of the total research external funds generated verse the full time equivalent faculty; (6) total expenses as a percent of external funds generated (includes centrally provided) is the ratio of the total expenses (including centrally provided) verse the total external funds generated; (7) Total faculty compensation as a percent of external funds generated is the ratio of the total faculty compensation verse the total external funds generated; (8) Clinical non-faculty compensation as a percentage of clinical external funds generated is the ratio of the clinical non-faculty salaries and benefits verse the clinical external funds generated; and (9) Clinical non-faculty non-compensation expense as a percentage of clinical external funds generated (excludes centrally provided) is the ratio of the clinical non-compensation expenses (excludes centrally provided) verse the clinical external funds generated.

To determine efficiency and investment, the following key ratios are used: (1) Total Faculty Compensation per Faculty Full Time Equivalent (FTE) is the ratio of the Total Faculty Compensation verse the Full Time Equivalent Faculty; (2) Total Non-Faculty Compensation per Faculty Full Time Equivalent (FTE) is the ratio of the Total Non-Faculty Compensation verse the Full Time Equivalent Faculty; (3) Total Non-Faculty Non-Compensation Expenses per Faculty Full Time Equivalent (FTE) (including Centrally Provided Services) is the ratio of the Total Non-Compensation Expenses verse the Full Time Equivalent Faculty; (4) Total Expenses per Faculty Full Time Equivalent (FTE) (including Centrally Provided Services) is the ratio of the Total Expenses verse the Full Time Equivalent Faculty; (5) Actual Funds Invested per Faculty Full Time Equivalent (FTE) is the ratio of Total Funds invested verse Full Time Equivalent Faculty; (6) Departmental Funds Invested per Faculty Full Time Equivalent (FTE) is the ratio of Departmental Funds Invested verse Full Time Equivalent Faculty; and (7) Centrally Provided Services per Faculty Full Time Equivalent (FTE) is the ratio of Centrally Provided Services verse Full Time Equivalent Faculty.

To determine productivity and efficiency for faculty compensation, the following key ratios are used: (1) Clinical external funds generated as a percent of total external funds generated is the ratio of clinical external funds generated verse total external funds generated; (2) Clinical faculty compensation as a percent of clinical external funds generated (includes faculty compensation reset) is the ratio of clinical faculty compensation verse total external funds generated; (3) Clinical faculty compensation as a percentage of total faculty compensation (includes faculty compensation reset) is the ratio of total non-compensation expenses verse full time equivalent faculty (FTE); (4) Clinical faculty compensation as a percentage of total faculty compensation (excludes faculty compensation reset) is the ratio of total expenses verse full time equivalent faculty (FTE); and (5) Clinical operating margin percentage of total operating margin is the ratio of clinical operating margin verse total operating margin.

To determine productivity for funds generated and funds invested, the following overall ratios are used: (1) Funds generated as a percentage of total funds (excludes teaching and supervision of residents) is the ratio of the total funds generated verse total sources of funds; (2) Funds invested as a percentage of total funds (excludes teaching and supervision of residents) is the ratio of the total funds invested verse total sources of funds; (3) Funds generated verse funds invested (excludes teaching and supervision of residents) is the ratio of the total funds generated verse total sources of funds invested; (4) Total funds generated per FTE (excludes teaching and supervision of residents) is the ratio of the total funds generated verse full time equivalent faculty; and (5) Funds invested per FTE (excludes teaching and supervision of residents) is the ratio of the total funds invested verse full time equivalent faculty.

For external funds generated per total faculty salary plus benefits, the following ratios are used: (6) Clinical efficiency is the ratio of the clinical revenue verse total faculty salaries and benefits; (7) Externally funded research efficiency is the ratio of the direct and indirect research revenue verse total faculty salaries and benefits; (8) Other external funds generated efficiency is the ratio of other funds generated verse total faculty salaries and benefits.

For contribution of external funds generated to Total Faculty Salary plus Benefits (excludes centrally provided services), the following ratios are used: (9) Clinical efficiency is the ratio of the clinical revenue minus the clinical expenses paid at department other than faculty salaries and benefits verse total faculty salaries and benefits; (10) Externally funded research efficiency is the ratio of the direct and indirect research revenue minus research expenses paid at department other than faculty salaries and benefits verse total faculty salaries and benefits; and (11) Other external funds generated efficiency is the ratio of other funds generated minus other academic expenses paid at department other than faculty salaries and benefits verse total faculty salaries and benefits.

For contribution of external funds generated to Total Faculty Salary plus Benefits (includes centrally provided services), the following ratios are used: (12) Clinical efficiency is the ratio of the clinical revenue minus the clinical expenses paid at department other than faculty salaries and benefits verse total faculty salaries and benefits; (13) externally funded research efficiency is the ratio of the direct and indirect research revenue minus research expenses paid at department other than faculty salaries and benefits verse total faculty salaries and benefits; and (14) Other external funds generated efficiency is the ratio of other funds generated minus other academic expenses paid at department other than faculty salaries and benefits verse total faculty salaries and benefits.

For dependency, funding mix (%) (excludes teaching and supervision of residents), the following ratios are used: (1) External funds generated by the clinical ratio of the clinical ratio verse the total sources of funds; (2) External funds generated by the research DER ratio of the direct search revenue verse the total sources of funds; (3) External funds generated by the research ICR ratio of the indirect search revenue verse the total sources of funds; (4) External funds generated by the tuition and fees ratio of the tuition and fees verse the total sources of funds; (5) Other external funds generated ratio of the other external generated verse the total source of funds; (6) Internal funds generated by sales and service ratio of the internally purchased services verse the total sources of funds; (7) Internal funds invested ratio of the funds is the ratio of the sum of the funds provided, expenses incurred and FG retained verse the total sources of funds; (8) Internal funds invested by the support between AMC operating units is the ratio of the support between AMC operating units verse the total sources of funds; and (9) Internal funds invested by the departmental investment is the ratio of the departmental investment verse the total sources of funds.

For efficiency-expense mix (%), the following ratios are used (1) The faculty salaries paid at the department ratio of the faculty salaries verse the total uses of funds; (2) The non-faculty salaries paid at the department ratio of the non-faculty salaries verse the total uses of funds; (3) The faculty benefits paid at the department ratio of the faculty benefits verse the total uses of funds; (4) The non-faculty benefits paid at the department ratio of the non-faculty benefits verse the total uses of funds; (5) The other paid at the department ratio of the other expenses paid at department verse the total uses of funds; (6) The efficiency of the expense mix (%) paid centrally is the ratio of the expenses paid centrally verse the total uses of funds; (7) The expenses as a percentage of external funds generated by the people for the faculty salaries and benefits is the ratio of the total faculty salaries and benefits verse external funds generated; (8) The expenses as a percentage of external funds generated by the people for the non-faculty salaries and benefits is the ratio of the total non-faculty salaries and benefits verse external funds generated; (9) The expenses as a percentage of external funds generated by others (including centrally provided) is the ratio of the sum of other expenses paid at department and expenses paid centrally verse external fund generated; (10) The expenses per full time equivalent for the total uses of funds per FTE (including centrally provided) is the ratio of total uses of funds verse the FTE faculty; (11) The expenses per full time equivalent for the non-faculty salaries and benefits per FTE is the ratio of the non-faculty salaries and benefits verse the FTE faculty; (12) The expenses per FTE for the total uses, excluding faculty salaries and benefits, per FTE is the ratio of the sum of the total expenses paid at department and the expenses paid centrally minus the faculty salaries and benefits verse the FTE faculty; (13) The faculty compensation paid by the school of medicine 12 from externally funded research is the ratio of the faculty salary paid out of the externally funded research verse the total faculty salaries; (14) The faculty compensation paid by the school of medicine 12 from other funds is the ratio of the faculty salary paid out of other academic funds verse the total faculty salaries; (15) The faculty compensation paid by the faculty practice plan is the ratio of the faculty salary paid out of faculty practice plan funds verse the total faculty salaries; and (16) The faculty compensation per FTE is the ratio of the faculty salaries and benefits verse the FTE faculty.

FIGS. 18A–D are exemplary charts of the key ratios for the clinical departments. The rows contain values for the different key ratios for the different departments listed in the columns.

Figure 19A:
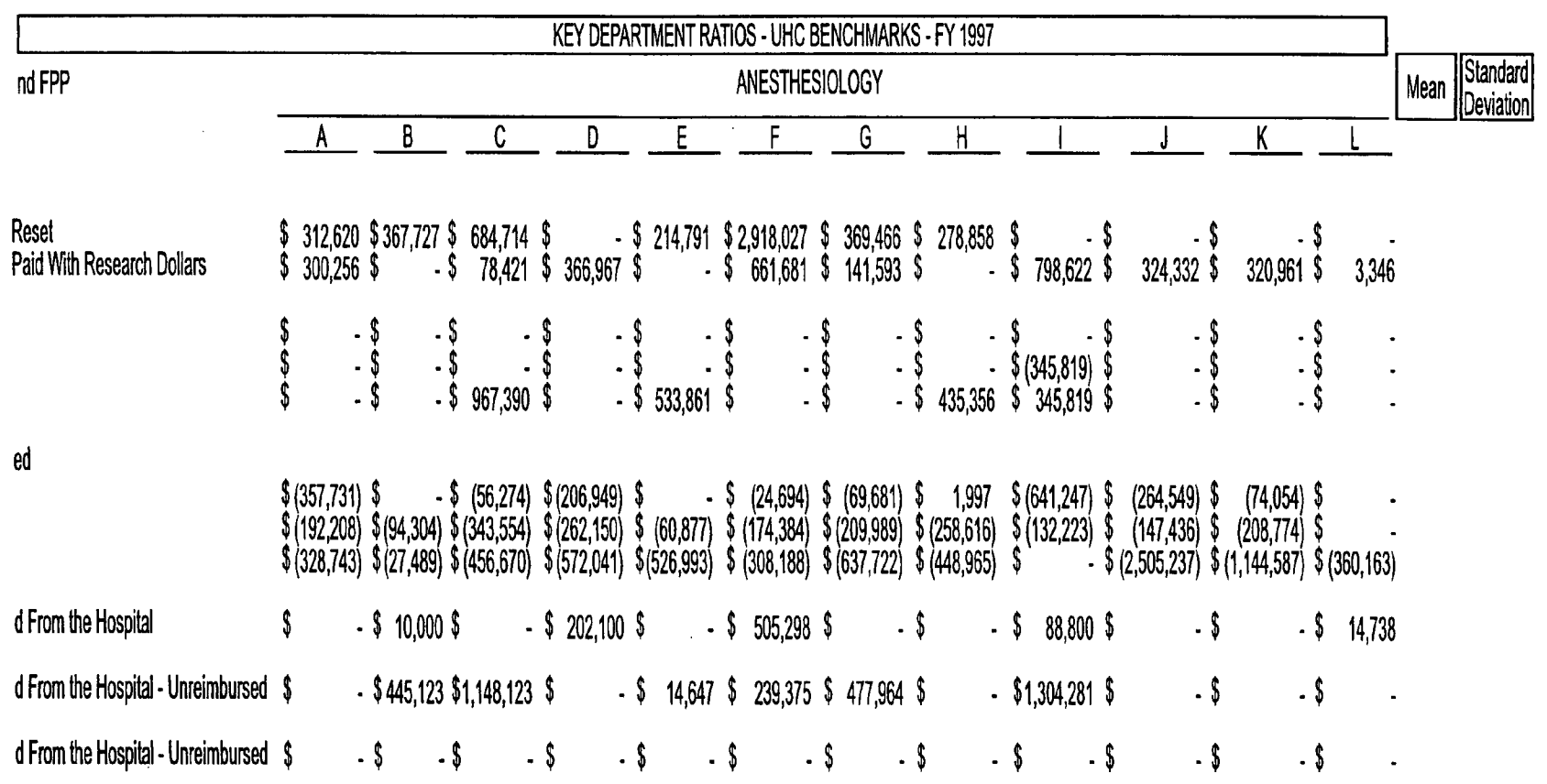

FIGS. 19A–B are exemplary charts of the key ratios for an anesthesiology department. Again, the rows contain values for the different key ratios for the different anesthesiology departments listed in the columns. The columns include the mean for the department as well as the standard deviation. In the preferred embodiment, each participant is given an institutional code. The purpose of the codes is to prevent a non-participant from gleaning participant-specific data from a report. Each participant receives the code key that identifies the participants.

Additional exemplary charts useful in carrying out the invention are attached in appendix A.

In order to gather and share all of the information as described above, at least portions of the invention are intended to be implemented on or over a network such as the Internet. An example of such a network is described in FIG. 20.

Figure 20:
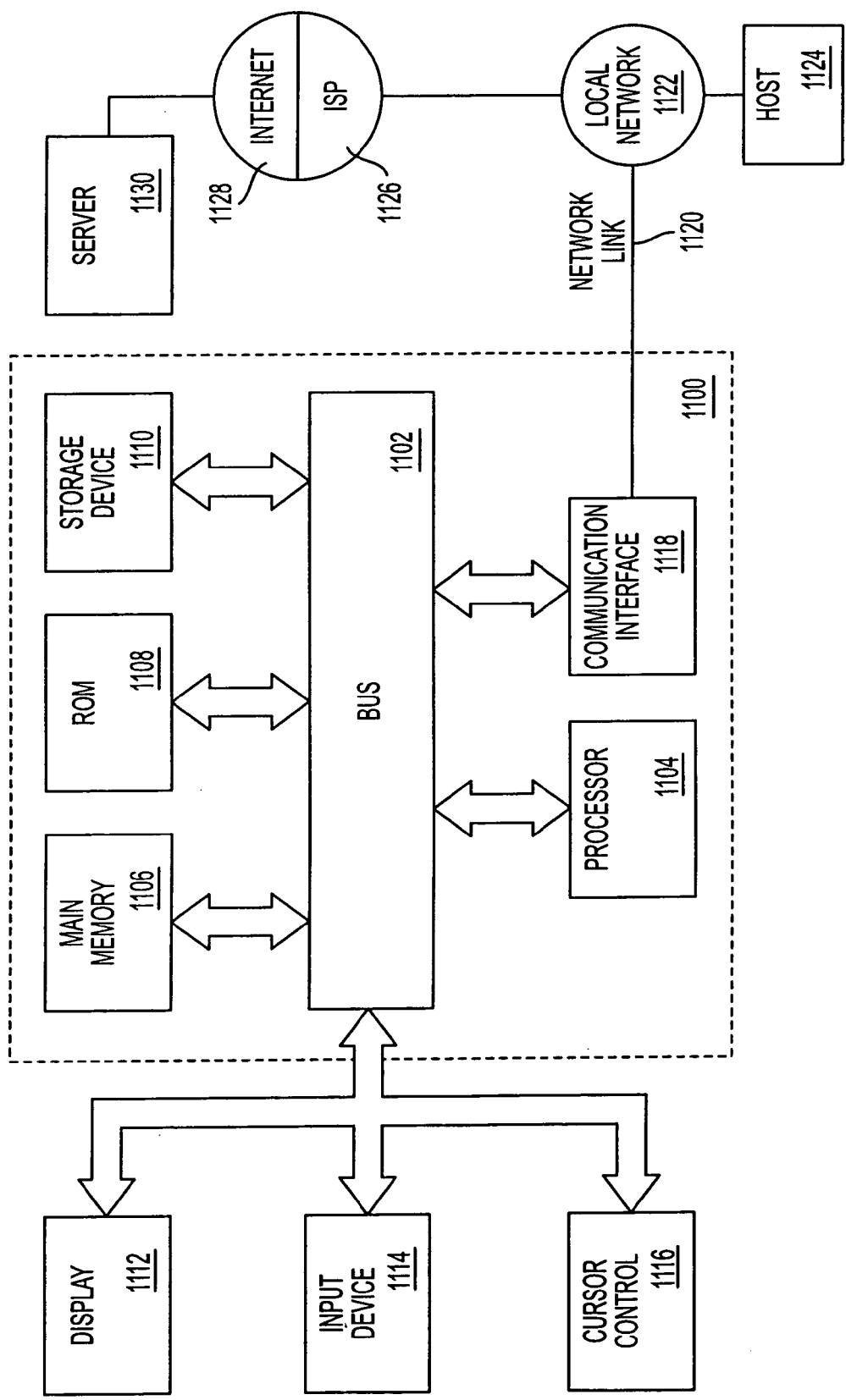

Referring to FIG. 20, a block diagram that illustrates a computer system 1100 upon which an embodiment of the invention may be implemented. Computer system 1100 includes a bus 1102 or other communication mechanism for communicating information, and a processor 1104 coupled with bus 1102 for processing information. Computer system 1100 also includes a main memory 1106, such as a random access memory (RAM) or other dynamic storage device, coupled to bus 1102 for storing information and instructions to be executed by processor 1104. Main memory 1106 also may be used for storing temporary variables or other intermediate information during execution of instructions to be executed by processor 1104. Computer system 1100 further includes a read only memory (ROM) 108 or other static storage device coupled to bus 1102 for storing static information and instructions for processor 1104. A storage device 1110, such as a magnetic disk or optical disk, is provided and coupled to bus 1102 for storing information and instructions.

Computer system 1100 may be coupled via bus 1102 to a display 1112, such as a cathode ray tube (CRT), for displaying information to a computer user. An input device 1114, including alphanumeric and other keys, is coupled to bus 1102 for communicating information and command selections to processor 1104. Another type of user input device is cursor control 116, such as a mouse, a trackball, or cursor direction keys for communicating direction information and command selections to processor 1104 and for controlling cursor movement on display 1112. This input device typically has two degrees of freedom in two axes, a first axis (e.g., x) and a second axis (e.g., y), that allows the device to specify positions in a plane.

Computer system 1100 operates in response to processor 1104 executing one or more sequences of one or more instructions contained in main memory 1106. Such instructions may be read into main memory 1106 from another computer-readable medium, such as storage device 1110.

Execution of the sequences of instructions contained in main memory 1106 causes processor 1104 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 1104 for execution. Such a medium may take many forms, including but not limited to, non-volatile media, volatile media, and transmission media. Non-volatile media includes, for example, optical or magnetic disks, such as storage device 1110. Volatile media includes dynamic memory, such as main memory 1106. Transmission media includes coaxial cables, copper wire and fiber optics, including the wires that comprise bus 102. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1104 for execution. For example, the instructions may initially be carried on a magnetic disk of a remote computer. The remote computer can load the instructions into its dynamic memory and send the instructions over a telephone line using a modem. A modem local to computer system 1100 can receive the data on the telephone line and use an infra-red transmitter to convert the data to an infra-red signal. An infra-red detector can receive the data carried in the infra-red signal and appropriate circuitry can place the data on bus 1102. Bus 1102 carries the data to main memory 1106, from which processor 1104 retrieves and executes the instructions. The instructions received by main memory 1106 may optionally be stored on storage device 1110 either before or after execution by processor 1104.

Computer system 1100 also includes a communication interface 1118 coupled to bus 1102. Communication interface 1118 provides a two-way data communication coupling to a network link 1120 that is connected to a local network 1122. For example, communication interface 1118 may be an integrated services digital network (ISDN) card or a modem to provide a data communication connection to a corresponding type of telephone line. As another example, communication interface 1118 may be a local area network (LAN) card to provide a data communication connection to a compatible LAN. Wireless links may also be implemented. In any such implementation, communication interface 1118 sends and receives electrical, electromagnetic or optical signals that carry digital data streams representing various types of information.

Network link 1120 typically provides data communication through one or more networks to other data devices. For example, network link 1120 may provide a connection through local network 1122 to a host computer 1124 or to data equipment operated by an Internet Service Provider (ISP) 1126. ISP 126 in turn provides data communication services through the world wide packet data communication network now commonly referred to as the "Internet" 1128. Local network 1122 and Internet 1128 both use electrical, electromagnetic or optical signals that carry digital data streams. The signals through the various networks and the signals on network link 1120 and through communication interface 1118, which carry the digital data to and from computer system 1100, are exemplary forms of carrier waves transporting the information.

Computer system 1100 can send messages and receive data, including program code, through the network(s), network link 1120 and communication interface 11118. In the Internet example, a server 1130 might transmit a requested code for an application program through Internet 1128, ISP 1126, local network 1122 and communication interface 1118. The received code may be executed by processor 1104 as it is received, and/or stored in storage device 1110, or other non-volatile storage for later execution. In this manner, computer system 1100 may obtain application code in the form of a carrier wave.

Computer workstation and computer systems such as those illustrated can be utilized to automate the analysis and reporting depicted herein.

Although the present invention has been described and illustrated in detail, it is clearly understood that the same is by way of illustration and example only and is not to be taken by way of limitation, the spirit and scope of the present invention being limited only by the terms of the appended claims and their equivalents.

What is claimed is:

1. An automated method of tracking the flow of funds in an academic health center including a school of medicine, a hospital and a clinical practice plan as participants, including the steps of:
    gathering data from each of the participants and other entities; and
    loading the data into processor, the processor carrying out the functions of:
    identifying, using the loaded data, all transactions across the participants and other entities;
    identifying, using the loaded data, all sources of funds provided for each department of a participant;
    identifying, using the loaded data, all uses of funds for each department of the participant;
    analyzing the funds flow among the participants; and
    generating a source of funds statement and uses of funds statement for each participant using the identified sources of funds and uses of funds, wherein
    the source of funds includes cash received and values received that are not cash, and
    the uses of funds include cash paid and values provided that are not cash values.

2. The method of claim 1, wherein the funds flow further comprise support funds, payment for services and unreimbursed expenses.

3. The method of claim 1, further comprising generating a departmental statement for each department of a participant based on the source of funds statement and uses of funds statement for each department.

4. The method of claim 3, further comprising generating ratios using the departmental statements.

5. A method of tracking the flow of funds in an academic health center including a school of medicine, a hospital and a clinical practice plan as participants, comprising the steps of:
    gathering data from each of the participants and other entities; and
    loading the data into processor, the processor carrying out the functions of:
    identifying, using the loaded data, all transactions across the participants and other entities;
    identifying, using the loaded data, all sources of funds provided for each department of a participant;
    identifying, using the loaded data, all uses of funds for said each department of the participant;
    analyzing the funds flow among the participants;
    generating a source of funds statement and uses of funds statement for each participant using the identified sources of funds and uses of funds;
    generating a departmental statement for each department of a participant based on the source of funds statement and uses of funds statement for each department; and
    generating ratios using the departmental statements outputting the source of funds statement and uses of funds statements to an output device of the computer, wherein
    the ratios include at least one ratio selected from the group consisting of: productivity and efficiency ratios, efficiency and investment ratios, productivity and efficiency for faculty compensation ratios, productivity for funds generated and funds invested ratios, external funds generated per total faculty salary plus benefits ratios, contribution of external funds generated to total faculty plus benefits excluding centrally provided services ratios; contribution of external funds generated to total faculty plus benefits including centrally provided services ratios; dependency funding mix percentage ratios; and efficiency expense mix percentage ratios.

6. The method of claim 4, further comprising generating a report for each participant comprising the departmental ratios.

7. The method of claim 4, further comprising including the step of comparing corresponding ratios for departments within a participant.

8. The method of claim 4, wherein the method further comprises a plurality of academic health centers and further comprising comparing the ratios for similar departments among a plurality of similarly situated participants.

9. The method of claim 1, wherein the step of identifying all transactions across the participants and other entities, further comprises quantifying the funds flows among the participants and other entities.

10. The method of claim 9, wherein the step of quantifying the funds flows among participants, further comprises identifying support and quantifying expected return for the support.

11. A system for tracking the flow of funds in an academic health center, comprising:
    a school of medicine, a hospital and a clinical practice plan as participants;
    a network connecting each of the participants;
    a processor for gathering data from each of the participants via the network and carrying out the functions of:
    identifying, using the gathered data, all transactions across said each of the participants;
    identifying, using the gathered data, all sources of funds provided for each department of a participant;
    identifying, using the gathered data, all uses of funds for each department of the participant;
    analyzing the funds flow among the participants; and
    generating a source of funds statement and uses of funds statement for each participant using the identified sources of funds and uses of funds, wherein
    the source of funds includes cash received and values received that are not cash, and the uses of funds include cash paid and values provided that are not cash values.

12. A system for tracking the flow of funds in an academic health center, comprising:
- a school of medicine, a hospital and a clinical practice plan as participants;
- a network connecting each of the participants; and
- a processor for gathering data from each of the participants and generating at least one report based on the data, wherein the data includes a list of all sources of funds and uses of funds for a each department of a participant, wherein the at least one report is selected from the group consisting of: custom triangle and supporting statements, standard triangle and supporting statements, customized departmental statements, standard department statements, departmental ratios by participants, ratios by department across participants, aggregate department sources and uses per FTE.

* * * * *